United States Patent
Campos et al.

(10) Patent No.: US 10,980,883 B2
(45) Date of Patent: Apr. 20, 2021

(54) TRIPLET FUSION UPCONVERSION FOR INFRARED-SENSITIZED PHOTOREDOX CHEMISTRY

(71) Applicants: The Trustees of Columbia University in the City of New York, New York, NY (US); President and Fellows of Harvard College, Cambridge, MA (US)

(72) Inventors: Luis M. Campos, Brooklyn, NY (US); Daniel N. Congreve, Cambridge, MA (US); Andrew Brian Pun, New York, NY (US); Kealan Fallon, New York, NY (US); Emily Marie Churchill, New York, NY (US); Tomislav Rovis, Scarsdale, NY (US); Benjamin Ravetz, New York, NY (US)

(73) Assignees: The Trustees of Columbia University in the City of New York, New York, NY (US); President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 16/351,370

(22) Filed: Mar. 12, 2019

(65) Prior Publication Data
US 2019/0275151 A1  Sep. 12, 2019

Related U.S. Application Data

(60) Provisional application No. 62/641,739, filed on Mar. 12, 2018.

(51) Int. Cl.
  *A61K 9/00* (2006.01)
  *A61K 41/00* (2020.01)
  *A61K 47/55* (2017.01)

(52) U.S. Cl.
  CPC ........ *A61K 41/008* (2013.01); *A61K 41/0042* (2013.01); *A61K 41/0071* (2013.01); *A61K 47/55* (2017.08)

(58) Field of Classification Search
  CPC .................................................... A61K 41/008
  See application file for complete search history.

(56) References Cited

U.S. PATENT DOCUMENTS

2016/0237343 A1  8/2016  Baldo et al.
2017/0236653 A1  8/2017  Hanson et al.
(Continued)

FOREIGN PATENT DOCUMENTS

CN         105503887 A      4/2016

OTHER PUBLICATIONS

Huang, Platinum Azaporphyrins for Near Infrared Organic Light Emitting Diodes, Solid-State and Organic Lighting 2013.*
(Continued)

*Primary Examiner* — Paul W Dickinson
(74) *Attorney, Agent, or Firm* — BakerHostetler

(57) ABSTRACT

Various exemplary photoreactions can be provided, including reactions generally based on triplet-triplet annihilation upconversion. Representative photosensitizers include PdPc (OBu)8 and PtTPTNP. Representative annihilators include FDPP and TTBP. Such exemplary photoreactions, systems and methods may be used in a variety of applications, including various biological or physical applications. Exemplary methods can also be provided for making or using such systems, photoreactions, kits including such systems, or the like.

18 Claims, 8 Drawing Sheets

FDPP

TTBP

(56) References Cited

U.S. PATENT DOCUMENTS

| | | |
|---|---|---|
| 2017/0274364 A1 | 9/2017 | Idriss et al. |
| 2017/0327389 A1 | 11/2017 | Kisailus et al. |

OTHER PUBLICATIONS

Neumann, Matthias et al., "Metal-Free, Cooperative Asymmetric Organophotoredox Catalysis with Visible Light**", Angew. Chem. Int. Ed., vol. 50, pp. 951-954, 2011.

Mashraqui, Sabir H. et al., "3-Methyl-2, 3-Dihydrobenzothiazoles as Reducing Agents. Dye Enhanced Photoreactions, Tetrahedron Letters," vol. 26, No. 11, pp. 1453-1456, 1985.

Natarajan, Palani et al., "Visible Light-Mediated intramolecular C—H Acylation of Diazonium Salts on N-(2-aminoarly) Benzoimines: A Facile Synthesis of 6-Aryiphenanthridines," Org. Chem. Front., vol. 3, pp. 1265-1270, 2016.

Pillai, V.N. Rajasekharan, "Photoremovable Protecting Groups in Organic Synthesis," Synthesis, vol. 4, pp. 1-27, Jan. 1980.

Pillai, V.N. Rajasekharan "Organic Photochemistry," vol. 9, Marcel Dekker, Inc., pp. 1-106, 1987.

Akiba et al., "Alkylation of benzothiazolines and the Stevens rearrangement of the resulting 2,3,3-trisubstituted benzothiazolium salts," Bull. Chem. Soc. Jpn., vol. 55, pp. 2976-2983 (1982).

Arias-Rotondo et al., "The photophysics of photoredox catalysis: a roadmap for catalyst design," Chem. Soc. Rev., vol. 45, pp. 5803-5820 (2016).

Askes et al., "Activation of a photodissociative ruthenium complex by triplet-triplet annihilation upconversion in liposomes," Angew. Chem. Int. Ed., vol. 53, pp. 1029-1033 (2014).

Benjamin et al., "Photoredox catalysis using infrared light via triplet fusion upconversion," Nature, vol. 565, pp. 343-346 (2019).

Bradforth SE et al, Excitation transfer in the core light-harvesting complex (LH-1) of Rhodobacter sphaeroides: an ultrafast fluorescence depolarization and annihilation study, Journal of Physical Chemistry vol. 99 / Issue 43 pp. 16179-16191 Oct. 1995.

Cambie et al., "Applications of continuous-flow photochemistry in organic synthesis, Material science, and water treatment," Chem. Rev., vol. 116, pp. 10276-10341 (2016).

Chen et al., "A porous metal-organic cage constructed from dirhodium paddlewheels: synthesis, structure and catalysis," J. Mater. Chem. A., vol. 3, pp. 20201-20209 (2015).

Chen et al., "Upconverting-nanoparticle-assisted photochemistry induced by low-intensity near-infrared light: how low can we go?," Chem. Eur. J., vol. 21, pp. 9165-9170 (2015).

Cheng YY et al, On the efficiency limit of triplet-triplet annihilation for photochemical upconversion, Physical Chemistry Chemical Physics, vol. 12 / Issue 1, pp. 66-71, Nov. 2009.

Cort et al., "Unprecedented detection of inherent chirality in uranyl-salophen complexes," Chem. Commun., vol. 0, pp. 2178-2179 (2003).

Deng et al., "Near-IR phosphorescent metalloporphyrin as a photochemical upconversion sensitizer," Chem. Commun., vol. 49, pp. 7406-7408 (2013).

El Roz KA et al, Photochemical upconversion in water, Chemical Communications, vol. 53 / Issue 85 pp. 11705-11708, Oct. 2017.

Farney et al., "Visible-Light sensitization of vinyl azides by transition-metal photocatalysis," Angew. Chem. Int. Ed., vol. 53, pp. 793-797 (2014).

Häring et al., Intragel photoreduction of aryl halides by green-to-blue upconversion under aerobic conditions, Chem. Commun., vol. 51, pp. 16848-16851 (2015).

Hartnett et al., "Effects of crystal morphology on singlet exciton fission in diketopyrrolopyrrole thin films," J. Phys. Chem. B, vol. 120, pp. 1357-1366 (2016).

He et al., "Ultralow-intensity near-infrared light induces drug delivery by upconverting nanoparticles," Chem. Commun., vol. 51, pp. 431-434 (2015).

Ischay et al., "Efficient visible light photocatalysis of [2+2] enone cycloadditions," J. Am. Chem. Soc., vol. 130, pp. 12886-12887 (2008).

Le et al., "A general small-scale reactor to enable standardization and acceleration of photocatalytic reactions," ACS Cent. Sci., vol. 3, pp. 647-653 (2017).

Li et al., "Copper-catalyzed enantioselective intramolecular conjugate addition/trapping reactions: synthesis of cyclic compounds with multichiral centers," Chem. Eur. J., vol. 13, pp. 3765-3771 (2007).

Li H et al., Synthesis of Yb3+/Ho3+ co-doped Bi2WO6 upconversion photocatalyst with highly improved visible light photocatalytic activity, Catalysis Communications, vol. 97, pp. 60-64, Jul. 2017.

Liu Q et al, Blue-emissive upconversion nanoparticles for low-power-excited bioimaging in vivo, Journal of the American Chemical Society, vol. 134 / Issue 11, pp. 5390-5397, Feb. 2012.

Lucky SS, Titania coated upconversion nanoparticles for near-infrared light triggered photodynamic therapy, ACS Nano, vol. 9 / Issue 1, pp. 191-205, 2015.

Mahboub et al., "Efficient infrared-to-visible upconversion with subsolar irradiance," Nano Lett., vol. 16, pp. 7169-7175 (2016).

Majek et al., "Application of visible-to-UV photon upconversion to photoredox catalysis: the activation of aryl bromides," Chem. Eur. J., vol. 21, pp. 15496-15501 (2015).

Mallo et al., "An improved experimental determination of external photoluminescence quantum efficiency," Adv. Mater., vol. 9, pp. 230-232, (1997).

Miyake et al., "Perylene as an organic photocatalyst for the radical polymerization of functionalized vinyl monomers through oxidative quenching with alkyl bromides and visible light," Macromolecules, vol. 47, pp. 8255-8261 (2014).

Park et al., "Upconverting nanoparticles: a versatile platform for wide-field two-photon microscopy and multi-modal in vivo imaging," Chem. Soc. Rev., vol. 44, pp. 1302-1317 (2015).

Prier et al., "Visible light photoredox catalysis with transition metal complexes: applications in organic synthesis," Chem. Rev., vol. 113, pp. 5322-5363 (2013).

Romero et al., "Organic photoredox catalysis," Chem. Rev., vol. 116, pp. 10075-10166 (2016).

Sasaki et al., "Near infrared-to-blue photon upconversion by exploiting direct S—T absorption of a molecular sensitizer," J. Mater. Chem., vol. C 5, pp. 5063-5067 (2017).

Schulze et al., "Photochemical upconversion: present status and prospects for its application to solar energy conversion," Energy Environ. Sci., vol. 8, pp. 103-125 (2015).

Simon YC et al., Low-power photon upconversion through triplet-triplet annihilation in polymers, Journal of Materials Chemistry vol. 221 Issue 39, pp. 20817-20830, Nov. 2009.

Singh-Rachford et al., "Low power visible-to-UV upconversion," J. Phys. Chem. A, vol. 113, pp. 5912-5917 (2009).

Singh-Rachford et al., "Pd(II) phthalocyanine-sensitized triplet-triplet annihilation from rubrene," J. Phys. Chem. A, vol. 112, pp. 3550-3556 (2008).

Singh-Rachford et al., "Photon upconversion based on sensitized triplet-triplet annihilation," Coord. Chem. Rev., vol. 254, pp. 2560-2573 (2010).

Singh-Rachford TN et al., Boron dipyrromethene chromophores: next generation triplet acceptors/annihilators for low power upconversion schemes, Journal of American Society vol. 130 / Issue 48, pp. 16164-16165, Nov. 2008.

Sivakumar et al., "Synthesis and characterization of diketopyrrolopyrrole-based D-(PI)-A-(PI)-D small molecules for organic solar cell applications," Heterocyclic Chem., vol. 54, pp. 1983-1994 (2017).

Smith et al., "Bioimaging: second window for in vivo imaging," Nat. Nanotechnol., vol. 4, pp. 710-711 (2009).

Sommer et al., "Photophysical properties of near-infrared phosphorescent p-extended platinum porphyrins," Chem. Mater., vol. 23, pp. 5296-5304 (2011).

Tucker et al., "Visible-light photoredox catalysis in flow," Angew. Chem. Int. Ed., vol. 51, pp. 4144-4147 (2012).

(56) References Cited

OTHER PUBLICATIONS

Viger et al., "Low power upconverted near-IR light for efficient polymeric nanoparticle degradation and cargo release," Adv. Mater., vol. 25, pp. 3733-3738 (2013).
Wu et al., "Solid-state infrared-to-visible upconversion sensitized by colloidal nanocrystals," Nature Photonics, vol. 10, pp. 31-34 (2016).
Zhang J et al, Efficient upconverting multiferroic core@shell photocatalysts: visible-to-near-infrared photon harvesting, ACS Applied Materials & Interfaces, vol. 9 / Issue 9, pp. 8142-8150, 2017.
Zhou et al., "An upconverted photonic nonvolatile memory," Nat. Commun., vol. 5, 4720 (2014).
Zhou et al., "Upconversion luminescent materials: advances and applications," Chem. Rev., vol. 115, pp. 395-465 (2015).

\* cited by examiner

FDPP

TTBP

PdPc(OBu)₈

PtTPTNP

FIGS. 3A-C
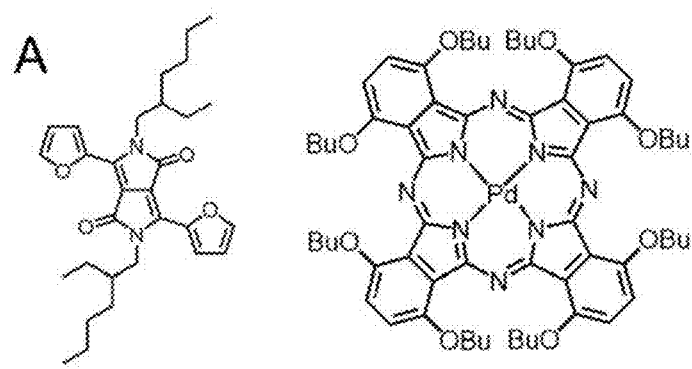
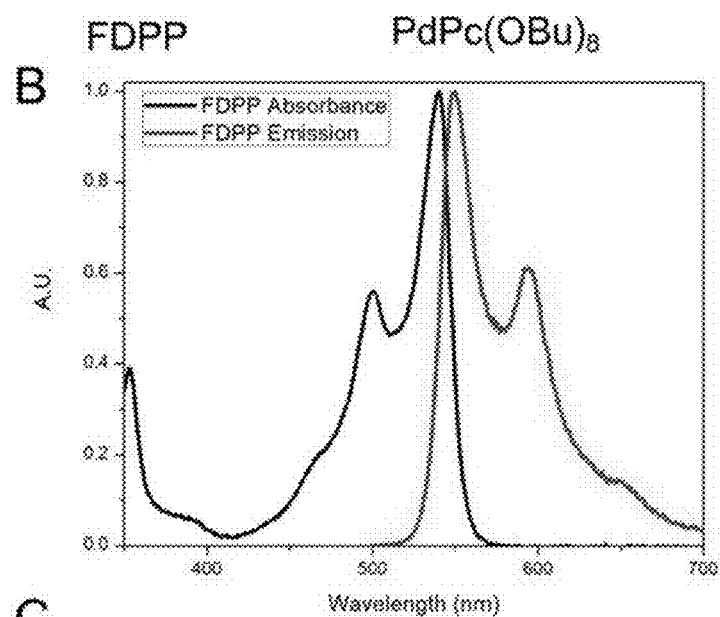
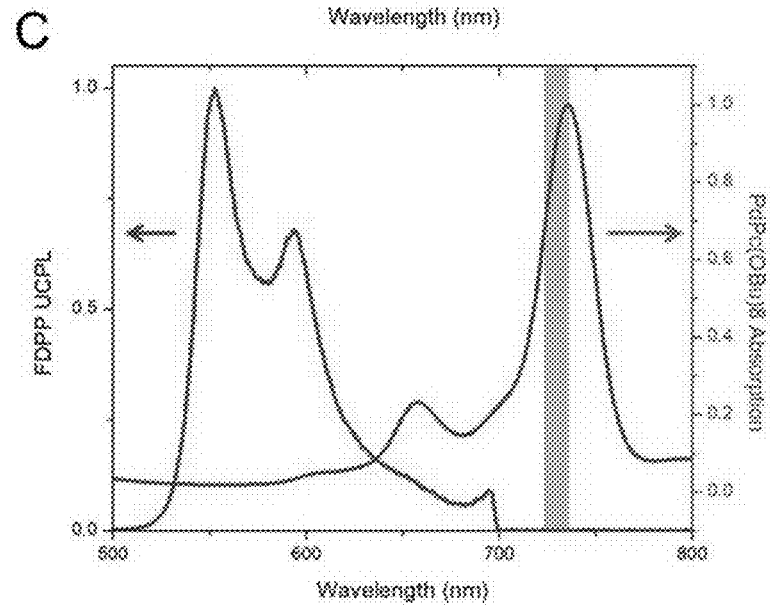

TRIPLET FUSION UPCONVERSION FOR INFRARED-SENSITIZED PHOTOREDOX CHEMISTRY

CROSS-REFERENCE TO RELATED APPLICATION(S)

This application relates to and claims priority from U.S. Patent Application No. 62/641,739, filed on Mar. 12, 2018, the entire disclosure of which is incorporated herein by reference.

STATEMENT REGARDING FEDERAL FUNDING

This invention was made with government support under Grant No. DMR-1351293 awarded by the National Science Foundation and under Grant No. GM125206 by the National Institutes of Health. The government has certain rights in the invention.

FIELD OF THE DISCLOSURE

Exemplary embodiments of the present disclosure relate to various photoreactions, including reactions generally based on a triplet-triplet annihilation upconversion.

BACKGROUND INFORMATION

Photon upconversion by photocatalysis is a process that converts two or more low-energy photons into a single high-energy visible photon via triplet fusion (also known as triplet-triplet annihilation). Photochemical transformations are limited by the energy of the incident light. Typical photoredox chemical transformations are induced by high energy light, such as ultraviolet (UV) or visible light.

Photocatalysis involves promoting synthetically useful transformations by converting light energy into chemical potential. Although discovered decades ago, this field has recently made significant advances in synthesis. Despite these recent achievements, the vast majority of photoredox chemistry still requires high energy blue/violet or ultraviolet (UV) light. This limits its applications in materials and biological chemistry due to the inherent disadvantages of high energy light: low material penetration and destructive photobleaching. For example, it is hard to achieve penetration with IR light in areas where visible light (or higher energy light) is blocked or has limited permittivity. High energy light can also be harmful to chemical reactions.

Thus, it may be beneficial to provide exemplary embodiments of the present disclosure relate to various photoreactions, including reactions generally based on a triplet-triplet annihilation upconversion which can overcome at least some of the deficiencies described herein above.

SUMMARY OF EXEMPLARY EMBODIMENTS

Exemplary embodiments of the present disclosure are directed to a combination of photosensitizer and annihilator for use in a composition and methods of triplet upconversion. By using incident IR light, it is possible to exploit a greater substrate scope, taking advantage of materials that would otherwise be destroyed by UV light.

One aspect of the exemplary embodiments of the present disclosure is directed to: a composition, comprising: a photosensitizer; and an annihilator able to accept triplet-triplet energy transfer from the photosensitizer, wherein (1) the photosensitizer is $PdPc(OBu)_8$ and the annihilator is a diketopyrrolopyrrole such as FDPP, or (2) the photosensitizer is PtTPTNP (Platinum tetraphenyltetranaphtho[2,3] porphyrin) and the annihilator is TTBP. Certain embodiments further comprise a cleavable moiety able to accept energy from the annihilator in the higher energy state to cause cleavage of the cleavable moiety; and a releasable moiety releasable from the composition upon cleavage of the cleavable moiety. In particular embodiments, the composition comprises a carrier material comprising the photosensitizer, the annihilator, and the cleavable moiety. In specific exemplary embodiments, the carrier material further comprises the releasable moiety; or a polymer; or a particle; or a film; or a polymeric micelle. In some embodiments, the particle has an average diameter of less than about 1 mm. In particular embodiments, the releasable moiety is a drug; or a caged species; or an anti-angiogenesis drug; or TNP-470; or Combretastatin A4; or an antiinflammatory drug; or dexamethasone; or an anticancer drug; or a chemotherapy drug; or doxorubicin; or topotecan; or verteporfin. In certain embodiments, the composition is contained within a subject; or contained within the eye of a subject; or contained within the skin of a subject; or contained within a tumor in a subject.

Another aspect of the exemplary embodiments of the present disclosure is directed to: a composition method, comprising: absorbing a photon in a photosensitizer; transferring energy from the photosensitizer to an annihilator via triplet-triplet energy transfer; producing a higher-energy state via triplet-triplet annihilation from the transferred energy in two annihilators; transferring energy from the annihilator in the higher-energy state to an active moiety via Forster resonance energy transfer; and causing a chemical reaction in the active moiety using the transferred energy, wherein (1) the photosensitizer is $PdPc(OBu)_8$ (Palladium 1,4,8,11,15,18,22,25-octabutoxy-29H,31H-phthalocyanine) and the annihilator is FDPP, or (2) the photosensitizer is PtTPTNP and the annihilator is TTBP. In certain embodiments, the active moiety is a cleavable moiety, and the chemical reaction is cleavage of the cleavable moiety. In further embodiments, cleaving the cleavable moiety causes release of a releasable moiety.

A further aspect of the exemplary embodiments of the present disclosure is directed to: a method, comprising: applying, to an eye of a subject, a composition comprising a photosensitizer, an annihilator able to accept triplet-triplet energy transfer from the photosensitizer, and a cleavable moiety able to accept energy from the annihilator in the higher energy state to cause cleavage of the cleavable moiety; and applying light to at least a portion of the eye to cause cleavage of the cleavable moiety, wherein (1) the photosensitizer is $PdPc(OBu)_8$ and the annihilator is FDPP or (2) the photosensitizer is PtTPTNP and the annihilator is TTBP In certain embodiments, the light is coherent; or the light is noncoherent; or the light is applied to the eye at an irradiance of at least about 1 mW/cm; or the light is applied to the eye at an irradiance of at least about 50 mW/cm; or the light is applied to the eye at an irradiance of no more than about 150 mW/cm. In particular embodiments, the subject has or is at risk for age-related macular degeneration; or the subject has or is at risk for retinoblastoma.

Another aspect of the exemplary embodiments of the present disclosure is directed to: method, comprising: applying, to an eye of a subject, a composition comprising a photosensitizer, an annihilator, a cleavable moiety, and a carrier material; and applying light to at least a portion of the eye, wherein absorption of light by the photosensitizer causes energy transfer to the annihilator and then to the cleavable moiety to cause cleavage of the cleavable moiety, wherein (1) the photosensitizer is PdPc(OBu)$_8$ and the annihilator is FDPP, or (2) the photosensitizer is PtTPTNP and the annihilator is TTBP.

Another aspect of the exemplary embodiments of the present disclosure is directed to: method, comprising: applying, to an eye of a subject, a composition comprising a carrier material comprising a photosensitizer having an absorption, an annihilator able to receive energy from the photosensitizer to produce an upconversion emission having higher energy than the absorption of the photosensitizer, and a cleavable moiety having an absorption overlapping with the upconversion emission from the annihilator; and applying light to at least a portion of the eye to cause cleavage of the cleavable moiety, wherein (1) the photosensitizer is PdPc(OBu)$_8$ and the annihilator is FDPP, or (2) the photosensitizer is PtTPTNP and the annihilator is TTBP.

These and other features, aspects, and advantages of exemplary embodiments of the present disclosure will become better understood with reference to the following detailed description when considered in association with the accompanying drawings and numbered paragraphs.

BRIEF DESCRIPTION OF THE DRAWINGS

Further objects, features and advantages of the present disclosure will become apparent from the following detailed description taken in conjunction with the accompanying Figures showing illustrative embodiments of the present disclosure, in which:

FIG. 3A is an exemplary illustration of structures of the exemplary annihilator (FDPP) and sensitizer (PdPc(OBu$_8$)) used in the working examples;

FIG. 3B is an exemplary graph of a normalized absorption (black) and emission (light) of FDPP in a dilute solution of toluene;

FIG. 3C is an exemplary graph of a normalized upconversion photoluminescence (UCPL) of a degassed solution of $4 \times 10^{-3}$M FDPP and $5 \times 10^{-5}$M PdPc(OBu)$_8$ in toluene shown in darker shade, with a 700 nm shortpass filter on the detector. Normalized absorbance spectra of PdPc(OBu)$_8$ shown in lighter shade, whereas the sample was irradiated with a 90 mA 730 nm laser diode, shown in shaded darker shade.

Figure 1:
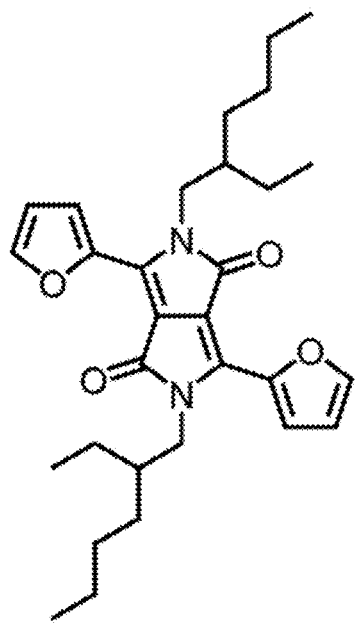
FIG. 1 is an illustration of annihilators (emitters) used in exemplary embodiments described herein.
Figure 1:
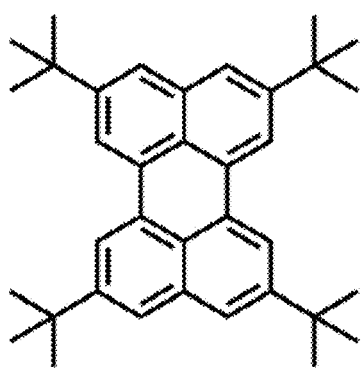
Figure 2:
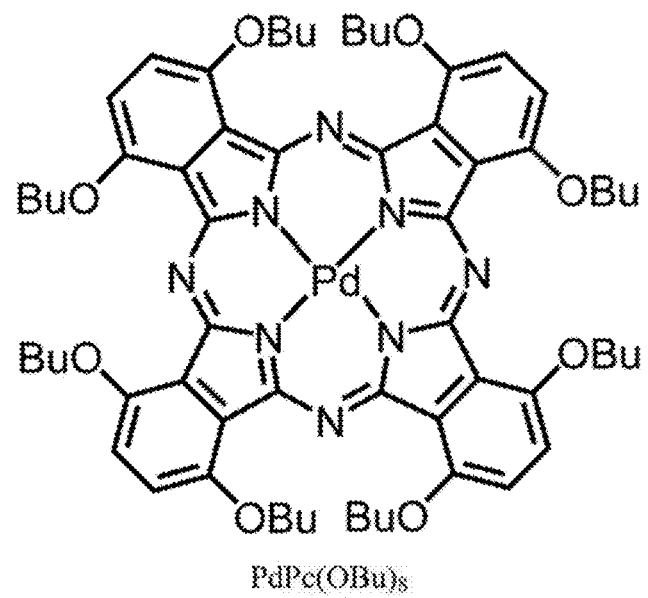
FIG. 2 is an exemplary illustration of sensitizers used in exemplary embodiments described herein.
Figure 2:
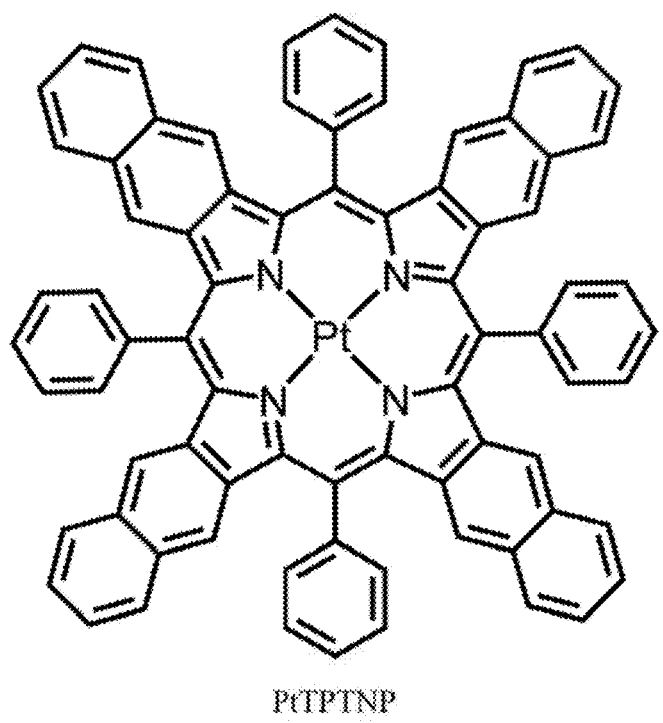

Throughout the drawings, the same reference numerals and characters, unless otherwise stated, are used to denote like features, elements, components, or portions of the illustrated embodiments. Moreover, while the present disclosure will now be described in detail with reference to the figures, it is done so in connection with the illustrative embodiments and is not limited by the particular embodiments illustrated in the figures and the appended claims.

DETAILED DESCRIPTION OF EXEMPLARY EMBODIMENTS

Reference will be made in detail to certain embodiments of the present disclosure, illustrating examples in the accompanying structures and figures. The present disclosure will be described in conjunction with the embodiments, including methods, materials and examples, such description is non-limiting and the present disclosure is intended to encompass all equivalents alternatives, and, modifications, either generally known, or incorporated here.

Unless otherwise defined, all technical and scientific terms used herein have the same meaning as commonly understood by one of ordinary skill in the art to which the present disclosure belongs. One of skill in the art will recognize many techniques and materials similar or equivalent to those described here, which could be used in the practice of the present disclosure. The described disclosure is not limited to the methods and materials described.

The exemplary embodiments of the present can be be better understood with reference to the following exemplary and non-limiting definitions.

As used herein, FDPP stands for 1,1'-bis-(2-ethyl-hexanyl), 2,2'-bis-(2-furanyl) diketopyrrolopyrrole, having the following structure:

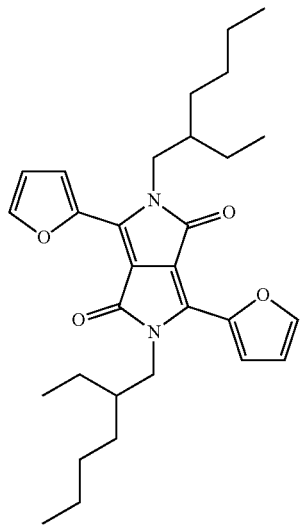 [SMILES: CCCCC(CC)CN1C(=O)C2=C(c3ccco3)N(CC(CC)CCCC)C(=O)C2=C1c1ccco1]

As used herein, FDPP has the following formula:

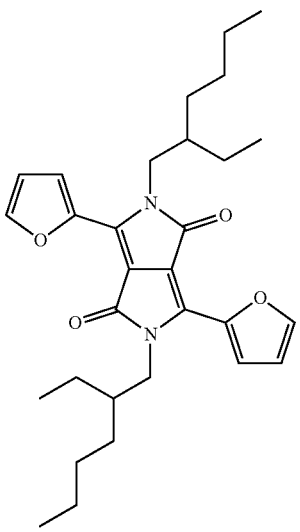 [SMILES: CCCCC(CC)CN1C(=O)C2=C(c3ccco3)N(CC(CC)CCCC)C(=O)C2=C1c1ccco1]

As used herein, TTBP has the following formula:

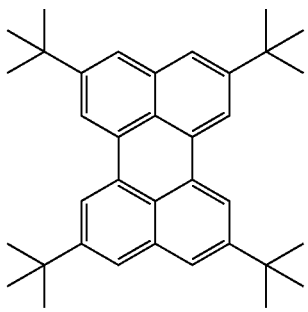 [SMILES: CC(C)(C)c1cc2cc(C(C)(C)C)cc3c4cc(C(C)(C)C)cc5cc(C(C)(C)C)cc(c(c1)c23)c54]

As used herein, PdPc(OBu)$_8$ (Palladium 1,4,8,11,15,18, 22,25-octabutoxy-29H,31H-phthalocyanine) has the following formula:

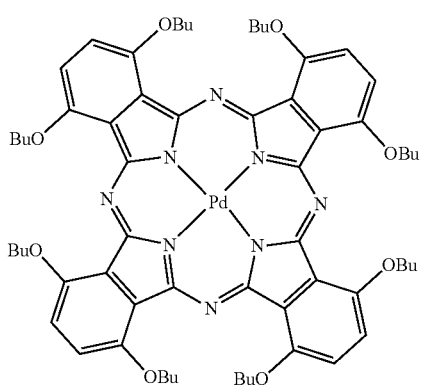

As used herein, PtTPTNP (Platinum tetraphenyltetranaphtho[2,3]porphyrin) has the following formula:

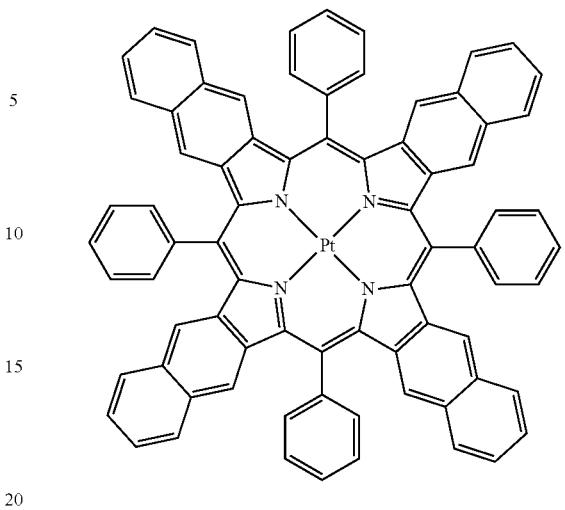

As used here and in the appended claims, the singular forms "a," "an," and "the" include plural reference unless the context clearly indicates otherwise.

The term "independently" is used herein to indicate that the variable, which is independently applied, varies independently from application to application. Thus, in a compound such as R"XYR", wherein R" is "independently carbon or nitrogen," both R" can be carbon, both R" can be nitrogen, or one R" can be carbon and the other R" nitrogen.

The term "alkyl," as used herein, unless otherwise specified, refers to a saturated straight, branched, or cyclic, primary, secondary, or tertiary hydrocarbons, including both substituted and unsubstituted alkyl groups. The alkyl group can be optionally substituted with any moiety that does not otherwise interfere with the reaction or that provides an improvement in the process, including but not limited to but limited to halo, haloalkyl, hydroxyl, carboxyl, acyl, aryl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphonate, either unprotected, or protected as necessary, as known to those skilled in the art, for example, as taught in Greene, et al., Protective Groups in Organic Synthesis, John Wiley and Sons, Second Edition, 1991, hereby incorporated by reference. Specifically included are $CF_3$ and $CH_2CF_3$.

In the text, whenever the term C(alkyl range) is used, the term independently includes each member of that class as if specifically and separately set out. The term "alkyl" includes $C_{1-22}$ alkyl moieties, and the term "lower alkyl" includes $C_{1-6}$ alkyl moieties. It is understood to those of ordinary skill in the art that the relevant alkyl radical is named by replacing the suffix "-ane" with the suffix "-yl".

The term "alkenyl" refers to an unsaturated, hydrocarbon radical, linear or branched, in so much as it contains one or more double bonds. The alkenyl group disclosed herein can be optionally substituted with any moiety that does not adversely affect the reaction process, including but not limited to but not limited to those described for substituents on alkyl moieties. Non-limiting examples of alkenyl groups include ethylene, methylethylene, isopropylidene, 1,2-ethane-diyl, 1,1-ethane-diyl, 1,3-propane-diyl, 1,2 propane-diyl, 1,3-butane-diyl, and 1,4-butane-diyl.

The term "alkynyl" refers to an unsaturated, acyclic hydrocarbon radical, linear or branched, in so much as it contains one or more triple bonds. The alkynyl group can be optionally substituted with any moiety that does not adversely affect the reaction process, including but not limited to those described above for alkyl moeities. Non-limiting examples of suitable alkynyl groups include ethynyl, propynyl, hydroxypropynyl, butyn-1-yl, butyn-2-yl, pentyn-1-yl, pentyn-2-yl, 4-methoxypentyn-2-yl, 3-methylbutyn-1-yl, hexyn-1-yl, hexyn-2-yl, and hexyn-3-yl, 3,3-dimethylbutyn-1-yl radicals.

The term "alkylamino" or "arylamino" refers to an amino group that has one or two alkyl or aryl substituents, respectively.

The term "protected" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art of organic synthesis, and are described, for example, in Greene et al., Protective Groups in Organic Synthesis, supra.

The term "aryl", alone or in combination, means a carbocyclic aromatic system containing one, two or three rings wherein such rings can be attached together in a pendent manner or can be fused. Non-limiting examples of aryl include phenyl, biphenyl, or naphthyl, or other aromatic groups that remain after the removal of a hydrogen from an aromatic ring. The term aryl includes both substituted and unsubstituted moieties. The aryl group can be optionally substituted with any moiety that does not adversely affect the process, including but not limited to but not limited to those described above for alkyl moieties. Non-limiting examples of substituted aryl include heteroarylamino, N-aryl-N-alkylamino, N-heteroarylamino-N-alkylamino, heteroaralkoxy, arylamino, aralkylamino, arylthio, monoarylamidosulfonyl, arylsulfonamido, diarylamidosulfonyl, monoaryl amidosulfonyl, arylsulfinyl, arylsulfonyl, heteroarylthio, heteroarylsulfinyl, heteroarylsulfonyl, aroyl, heteroaroyl, aralkanoyl, heteroaralkanoyl, hydroxyaralkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, and heteroarylalkenyl, carboaralkoxy.

The terms "alkaryl" or "alkylaryl" refer to an alkyl group with an aryl substituent. The terms "aralkyl" or "arylalkyl" refer to an aryl group with an alkyl substituent.

The term "halo," as used herein, includes chloro, bromo, iodo and fluoro.

The term "acyl" refers to a carboxylic acid ester in which the non-carbonyl moiety of the ester group is selected from straight, branched, or cyclic alkyl or lower alkyl, alkoxyalkyl including but not limited to methoxymethyl, aralkyl including but not limited to benzyl, aryloxyalkyl such as phenoxymethyl, aryl including but not limited to phenyl optionally substituted with halogen (F, Cl, Br, I), alkyl (including but not limited to $C_1$, $C_2$, $C_3$, and $C_4$) or alkoxy (including but not limited to $C_1$, $C_2$, $C_3$, and $C_4$), sulfonate esters such as alkyl or aralkyl sulphonyl including but not limited to methanesulfonyl, the mono, di or triphosphate ester, trityl or monomethoxytrityl, substituted benzyl, trialkylsilyl (e.g., dimethyl-t-butylsilyl) or diphenylmethylsilyl. Aryl groups in the esters optimally comprise a phenyl group. The term "lower acyl" refers to an acyl group in which the non-carbonyl moiety is lower alkyl.

The terms "alkoxy" and "alkoxyalkyl" embrace linear or branched oxy-containing radicals having alkyl moieties, such as methoxy radical. The term "alkoxyalkyl" also embraces alkyl radicals having one or more alkoxy radicals attached to the alkyl radical, that is, to form monoalkoxyalkyl and dialkoxyalkyl radicals. The "alkoxy" radicals can be further substituted with one or more halo atoms, such as fluoro, chloro or bromo, to provide "haloalkoxy" radicals. Examples of such radicals include fluoromethoxy, chloromethoxy, trifluoromethoxy, difluoromethoxy, trifluoroethoxy, fluoroethoxy, tetrafluoroethoxy, pentafluoroethoxy, and fluoropropoxy.

The term "alkylamino" denotes "monoalkylamino" and "dialkylamino" containing one or two alkyl radicals, respectively, attached to an amino radical. The terms arylamino denotes "monoarylamino" and "diarylamino" containing one or two aryl radicals, respectively, attached to an amino radical. The term "aralkylamino", embraces aralkyl radicals attached to an amino radical. The term aralkylamino denotes "monoaralkylamino" and "diaralkylamino" containing one or two aralkyl radicals, respectively, attached to an amino radical. The term aralkylamino further denotes "monoaralkyl monoalkylamino" containing one aralkyl radical and one alkyl radical attached to an amino radical.

The term "heteroatom," as used herein, refers to oxygen, sulfur, nitrogen and phosphorus.

The terms "heteroaryl" or "heteroaromatic," as used herein, refer to an aromatic that includes at least one sulfur, oxygen, nitrogen or phosphorus in the aromatic ring.

The term "heterocyclic," "heterocyclyl," and cycloheteroalkyl refer to a nonaromatic cyclic group wherein there is at least one heteroatom, such as oxygen, sulfur, nitrogen, or phosphorus in the ring.

Nonlimiting examples of heteroaryl and heterocyclic groups include furyl, furanyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbazolyl, oxazolyl, thiazolyl, isothiazolyl, 1,2,4-thiadiazolyl, isooxazolyl, pyrrolyl, quinazolinyl, cinnolinyl, phthalazinyl, xanthinyl, hypoxanthinyl, thiophene, furan, pyrrole, isopyrrole, pyrazole, imidazole, 1,2,3-triazole, 1,2,4-triazole, oxazole, isoxazole, thiazole, isothiazole, pyrimidine or pyridazine, and pteridinyl, aziridines, thiazole, isothiazole, 1,2,3-oxadiazole, thiazine, pyridine, pyrazine, piperazine, pyrrolidine, oxaziranes, phenazine, phenothiazine, morpholinyl, pyrazolyl, pyridazinyl, pyrazinyl, quinoxalinyl, xanthinyl, hypoxanthinyl, pteridinyl, 5-azacytidinyl, 5-azauracilyl, triazolopyridinyl, imidazolopyridinyl, pyrrolopyrimidinyl, pyrazolopyrimidinyl, adenine, N6-alkylpurines, N6-benzylpurine, N6-halopurine, N6-vinypurine, N6-acetylenic purine, N6-acyl purine, N6-hydroxyalkyl purine, N6-thioalkyl purine, thymine, cytosine, 6-azapyrimidine, 2-mercaptopyrmidine, uracil, N5-alkylpyrimidines, N5-benzylpyrimidines, N5-halopyrimidines, N5-vinylpyrimidine, N5-acetylenic pyrimidine, N5-acyl pyrimidine, N5-hydroxyalkyl purine, and N6-thioalkyl purine, and isoxazolyl. The heteroaromatic group can be optionally substituted as described above for aryl. The heterocyclic or heteroaromatic group can be optionally substituted with one or more substituent selected from halogen, haloalkyl, alkyl, alkoxy, hydroxy, carboxyl derivatives, amido, amino, alkylamino, dialkylamino. The heteroaromatic can be partially or totally hydrogenated as desired. As a nonlimiting example, dihydropyridine can be used in place of pyridine. Functional oxygen and nitrogen groups on the heterocyclic or heteroaryl group can be protected as necessary or desired. Suitable protecting groups are well known to those skilled in the art, and include trimethylsilyl, dimethylhexylsilyl, t-butyldimethylsilyl, and t-butyldiphenylsilyl, trityl or substituted trityl, alkyl groups, acyl groups such as acetyl and propionyl, methanesulfonyl, and p-toluenelsulfonyl. The heterocyclic or heteroaromatic group can be substituted with any moiety that does not adversely affect the reaction, including but not limited to but not limited to those described above for aryl.

The term "pharmaceutically acceptable salt or prodrug" is used throughout the specification to describe any pharmaceutically acceptable form (such as an ester) compound which, upon administration to a patient, provides the compound. Pharmaceutically acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art. Pharmaceutically acceptable prodrugs refer to a compound that is metabolized, for example hydrolyzed or oxidized, in the host to form the compound of the present invention. Typical examples of prodrugs include compounds that have biologically labile protecting groups on functional moieties of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, or dephosphorylated to produce the active compound. The prodrug forms of the compounds of this invention can possess antiviral activity, can be metabolized to form a compound that exhibits such activity, or both.

The term "photocleavable" is meant to refer to a compound or composition that is cleavable by light, i.e., wherein exposure to (absorbance of) light of a suitable wavelength and energy causes the cleavage of one or more covalent bonds. In certain embodiments, the light is in the visible range (e.g., a wavelength or wavelengths from about 390 nm to about 700 nm). In certain embodiments, a photocleavable linker is cleavable by exposure to light at a wavelength of about 400 nm-500 nm, or, more specifically, about 405 nm.

Many photocleavable moieties are known in the art; see, for example, V. N. R. Pillai, Synthesis, 1 (1980) and V. N. R. Pillai, "Photolytic Deprotection and Activation of Functional Groups," Org. Photochem., 9, 225-323 (1987). Examples of photocleavable moieties include o-nitrobenzyl phenacyl, nitrosulfenyl moieties, nitoroindolines, and coumarins, including aminocoumarins. (Coumarin-4-yl)methyl esters (CM-A) are caged compounds that, upon excitation, release the masked biologically active acid HA and the highly fluorescent (coumarin-4-yl)methyl alcohol CM-OH very rapidly and in part with high efficiency. Preferred photocleavable moieties include the dimethoxynitrobenzyl (DMNB) moiety or a derivative or analog thereof. It will be appreciated that many monovalent photocleavable moieties known in the art can be adapted for use as bivalent photocleavable linkers in the compounds described herein.

In certain embodiments, the photocleavable moiety is cleavable by light capable of penetrating a cell wall, a tissue, or an organ (including skin). In preferred embodiments, the photocleavable moiety can be cleaved by a wavelength (or wavelengths) of light which will not cause substantial damage to cells or cellular components such as proteins, nucleic acids, and the like. In certain embodiments, the light is in the visible range (e.g., a wavelength or wavelengths from about 390 nm to about 700 nm). In certain embodiments, a photocleavable linker is cleavable by exposure to light at a wavelength of about 400 nm-500 nm, or, more specifically, about 405 nm. The photocleavable linker preferably has a high quantum yield for photochemical cleavage. The light may be supplied by any light source known in the art, e.g., sunlight, incandescent bulb, fluorescent bulb, halogen bulb, light-emitting diode, laser, and the like. In certain embodiments, the photocleavable linker may be cleaved by two-photon activation with IR or near-IR wavelengths, which permits three-dimensional spatial specificity in depth in tissue. Exemplary moieties capable of two-photon photolysis include nitroindolines and aminocoumarins.

I. Infrared Upconversion Sensitized Photochemistry

There have been many advancements in photochemistry, especially over the past decade. This process is now being exploited in process chemistry. The vast majority of these photochemical reactions require high energy light, which has very low transmission in solution. As disclosed herein, IR sensitization allows for deeper penetration into a solution, leading to more efficient reactions. Infrared upconversion sensitized photochemistry can also increase substrate scope, in that it will allow the use of starting materials that are sensitive to high energy light. Different from flow chemistry and photoswitches, the present disclosure herein utilizes IR radiation to increase photon exposure and activate molecules.

Current technologies require very high energy light, typically blue/violet or ultraviolet, in order to excite the catalysts necessary to perform these photoredox reactions. Using low energy infrared light allows the user to catalyze reactions that contain materials that would typically be sensitive to high energy light. It is envisioned that the greatest impact of the present disclosure herein is in biological systems, where the user can take advantage of the fact that IR light has far greater dermal penetration than blue/violet or UV light. This technology can be used to catalyze reaction through skin after activation with an IR light source. The process may be used to replace UV curing of dental composites.

Exemplary embodiments of the present disclosure described herein relate to various photoreactions, including reactions generally based on a triplet-triplet annihilation upconversion disclosed herein demonstrates that photoredox reactions with large chemical potentials can proceed with low-energy IR radiation when paired with the appropriate upconversion system. In one exemplary embodiment, Eosin Y as a photocatalyst is used, which absorbs light up to 560 nm (green light). The incident IR light is not high enough energy to excite this photocatalyst on its own. Instead, it excites the triplet photosensitizer in solution. Then, energy transfer from the photosensitizer to the organic chromophores generates a triplet excited chromophore. Two triplet excited chromophores collide and combine, to form a higher energy singlet, which decays via fluorescence to give off a higher energy photon of light down to 525 nm. This fluorescence is high enough energy to excite the photocatalyst, which subsequently catalyzes the reaction. The present disclosure can be used to overcome various limitations faced by current techniques. In one case, in-vivo applications can benefit, where non-toxic starting materials, or a prodrug, can be dosed to the entire body and activated with IR radiation via the merged upconversion and photoredox system disclosed herein to generate the active drug in a spatially controlled manner. This could not be achieved with current photoredox chemistry, because it requires high energy light which is not capable of penetrating the skin.

It should be understood that, as is known to those of ordinary skill in the art, terms such as "singlet" or "triplet" generally refer to the electronic state of a molecule, not to the number of electrons that are present within the molecule. For example, in a singlet state, all of the electron spins within a molecule are typically paired such that the net spin the molecule has is 0, while in a triplet state, the molecule may have unpaired electrons present such that the net spin the molecule has is 1. Absorption of energy by a molecule, e.g., through absorption of a photon, may result in an electron from the molecule being "raised" from a lower energy state (or shell) to a higher energy state (or shell), which may alter the net spin of the molecule, while emission or transfer of that energy may allow a higher-energy electron to return to a lower state.

In addition, the energy from the higher energy state of the annihilator, after triplet-triplet annihilation, may be transmitted to another moiety, such as to a cleavable moiety. The cleavable moiety may then be cleaved as a result of the energy from the annihilator. The energy transfer from the annihilator to the cleavable moiety may occur through a variety of processes. For example, in one set of embodiments, energy transfer may occur via Forster resonance energy transfer (FRET). Surprisingly, FRET processes have not previously been suggested as a mechanism for transferring energy from an annihilator to a cleavable moiety. In FRET, energy transfer may occur between two molecules (which may be light-sensitive molecules or chromophores), through processes such as dipole-dipole coupling of the molecules. In some cases, transfer of energy may occur through emission (e.g., of a photon) by the annihilator and its absorption by the cleavable moiety; thus, for instance, the upconversion emission spectrum of the annihilator may overlap with the absorption spectrum of the cleavable moiety in order to facilitate such transfer.

Cleavage of the cleavable moiety can cause breakage of one or more bonds (e.g., covalent bonds) within or linked to the cleavable moiety. In some cases, cleavage of the cleavable moiety may cause a portion of the moiety to become separated or released, e.g., as a releasable moiety. Thus, in such a fashion, absorption of a photon (e.g., via a photosensitizer) may produce a chain of events that results in the release of releasable moiety. Accordingly, by controlling the incident light, the release of releasable moiety can be controlled as desired. However, it should be understood that a releasable moiety is not required, for example, cleavage of the cleavable moiety may result in other chemical or structural changes within the cleavable moiety. In addition, it should be understood that the energy may be transferred to other active moieties instead of a cleavable moiety, e.g., the energy may result in photoisomerization, rearrangement, photocycloaddition, or other chemical reactions.

Thus, in one set of exemplary embodiments, a composition can be provided comprising a photosensitizer, an annihilator, and a cleavable moiety (or other active moiety) may be applied to a region (e.g., within a sample, within a subject, etc.), and light applied to the region (or at least a portion of the region) in order to cause cleavage of the cleavable moiety, for example, to cause a chemical change, to release a releasable moiety, or the like. As mentioned, other active moieties may also be used. For example, if the active moiety is a cleavable moiety, the releasable moiety may be a drug, and light may applied to thereby cause release of the drug.

As another non-limiting example, the releasable moiety can be a tracer (for example, a radioactive tracer, an inert molecule, a detectable entity, etc.) that can be introduced to a system (e.g., a biological system such as a cell or an organism, or a non-biological system such as a polymer), and the tracer released at an appropriate time (e.g., through applying light), for instance, instead of being instantly released upon administration or incorporation of the composition. The tracer may then be detected using any suitable technique, e.g., fluorescence, radioactivity, biological assay, chemical or enzymatic activity, etc.

In some exemplary cases, components such as the photosensitizer, the annihilator, and/or the cleavable moiety may be contained within a suitable carrier material. In some cases, the carrier material may hold the photosensitizer, the annihilator, and/or the cleavable moiety in close proximity to each other, e.g., to allow for electron and/or photon transfers to occur as discussed herein. For example, in one embodiment, the photosensitizer, the annihilator, and/or the cleavable moiety may be contained within a particle, such as a microparticle or a nanoparticle. In some cases, the particle may contain an environment (e.g., a hydrophobic or non-polar environment), for instance, to keep the photosensitizer, the annihilator, or the cleavable moiety in close proximity, to facilitate transfer of electrons and/or photons, etc.

For example, in one set of exemplary embodiments, the composition includes a photosensitizer.

II. Photosensitizers

The photosensitizer can be any composition that is able to absorb a photon to produce a higher energy state. The higher energy state is a singlet excited state in some embodiments. The energy may be transferrable to the annihilator. The photosensitizer is able to absorb a wavelength of infrared light (e.g., about 650 nm to about 1350 nm, or about 700 nm to about 1200 nm, etc.).

As non-limiting examples, the photosensitizer may have an excitation wavelength of at least about 360 nm, at least about 370 nm, at least about 380 nm, at least about 390 nm, at least about 400 nm, at least about 410 nm, at least about 420 nm, at least about 430 nm, at least about 440 nm, at least about 450 nm, etc. In some embodiments, the photosensitizer has an excitation wavelength of no more than about 700 nm, no more than about 690 nm, no more than about 680 nm, no more than about 670 nm, no more than about 660 nm, no more than about 650 nm, no more than about 640 nm, no more than about 630 nm, no more than about 620 nm, no more than about 610 nm, no more than about 600 nm, etc. Combinations of any of these are also possible; for instance, the photosensitizer may have an excitation wavelength of between about 360 nm and about 700 nm, between 400 nm and about 700 nm, between 450 nm and about 700 nm, etc. It should be understood that the photosensitizer can be excited by light of a single wavelength (e.g., monochromatic light, such as would be supplied by a laser), or by light of different wavelengths (e.g., from a light source producing a spectrum of wavelengths).

In some exemplary embodiments, the photosensitizer is a compound that can be excited to the triplet excited state. In some cases, the photosensitizer is directly excited to an excited triplet state, although in other embodiments, the photosensitizer is first excited to an excited singlet state, and intersystem crossing or other suitable processes may convert the excited singlet state to an excited triplet state. Thus, the photosensitizer may exhibit, in some embodiments, absorption of the excitation light, a relatively high yield of intersystem crossing (ISC) for efficient production of the triplet state, and a relatively long triplet lifetime state (e.g., greater than microseconds). In addition, in some embodiments, the photosensitizer may have a large e max at the excitation wavelength in the visible-to-near-IR region of the spectrum. The triplet excited state of the photosensitizer can also be greater than the triplet acceptor energy of the annihilator in some cases.

The photosensitizer may be in close proximity to an annihilator. For instance, the photosensitizer can be positioned such that energy may be transferred from the photosensitizer to the annihilator through a triplet-triplet energy transfer (TTET) process. In some cases, the photosensitizer can be directly covalently bound to an annihilator, or indirectly immobilized to an annihilator, e.g., through covalent binding to one or more linking entities between the photosensitizer and the annihilator. However, in other embodiments, the photosensitizer and the annihilator may not necessarily be immobilized using covalent bonds to each other, but are physically positioned within close proximity, e.g., such that electrons may be transferred between the photosensitizer and the annihilator. For example, both the photosensitizer and the annihilator may be contained within a carrier material, for example, contained within a liposome, a polymer film, a particle, a micelle, or the like.

Representative classes of photosensitizers include phthalocyanines and conjugated polymers. In one embodiment, the photosensitizer is porphyrin or a porphyrin derivative, e.g., a transition metal-porphyrin such as a Pt porphyrin or a Pd porphyrin. Specific non-limiting examples of photosensitizers include palladium octaethylporphyrin (PdOEP), platinum octaethylporphyrin (PtOEP), diiodoboron dipyrromethene (BODIPY-1), tris(2-phenylpyridinato-C,N) iridium (III) (Ir(ppy)3), platinum (II) tetraphenyltetrabenzoporphyrin (PtTPBP), 1,4,8,11,15,18,22,25-octabutoxyphthalocyaninato-palladium (II) (PdPc(OBu)8), 2,6-diiodo-Bodipy, etc.

In another embodiment, the photosensitizer is BODIPY (4,4-difluoro-4-bora-3a,4a-diaza-s-indacene) or a BODIPY derivative, such as BODIPY FL, BODIPY R6G, BODIPY TMR, BODIPY581/591, BODIPY TR, BODIPY 630/650, BODIPY650/665, etc.

Representative photosensitizers include the PdPc(OBu)$_8$ and PtTPTNP (Platinum tetraphenyltetranaphtho[2,3]porphyrin).

Analogs of the photosensitizers described above, where one of more of the aromatic or heteroaromatic rings are functionalized with one or two L moieties as described herein, or where different alkyl or alkoxy moieties are present than the specific moieties in the individually-listed photosensitizers.

III. Annihilators

The annihilator may be any composition that is able to accept triplet-triplet energy transfer from the photosensitizer. In some cases, the annihilator is able to upconvert the energy transferred from the photosensitizer via triplet-triplet annihilation. The annihilator may also be able to transfer the upconverted energy to the cleavable moiety, e.g., using FRET or other suitable processes. In some cases, the annihilator may have a fluorescent quantum yield of near 1. In some embodiments, the photosensitizer molecule is chosen so that its singlet excited state lies below that of the annihilator's singlet state while the photosensitizer's triplet state lies above that of the annihilator's. Thus, the singlet and triplet excited states of the photosensitizer can be nested between the singlet and triplet excited states of the annihilator, at least in some cases.

Typically, during upconversion, two molecules (e.g., two annihilator molecules), each in a triplet state, may react to produce two singlet states. This can generally be referred to as triplet-triplet annihilation (TTA). An interaction between the two molecules may be able to excite one of them to a higher energy singlet state, while the other molecule enters a lower energy singlet state. Essentially, the energy is combined together into one molecule to cause it to reach a higher, upconverted energy state, at the expense of the other molecule, which thereby returns to the ground state (or at least a lower energy state). Thus, triplet-triplet annihilation can be used to produce energy levels that are higher ("upconverted") than the energy from the initial incident photons. This may be advantageously used, for example, in situations where higher energy states are desired, without using photons having too high of an energy level.

In some exemplary embodiments, the annihilator has an emission wavelength of at least about 360 nm, at least about 370 nm, at least about 380 nm, at least about 390 nm, at least about 400 nm, at least about 410 nm, at least about 420 nm, at least about 430 nm, at least about 440 nm, at least about 450 nm, etc. In some embodiments, the photosensitizer has an excitation wavelength of no more than about 700 nm, no more than about 690 nm, no more than about 680 nm, no more than about 670 nm, no more than about 660 nm, no more than about 650 nm, no more than about 640 nm, no more than about 630 nm, no more than about 620 nm, no more than about 610 nm, no more than about 600 nm, etc. Exemplary combinations of any of these wavelengths are also possible in other embodiments; for instance, the photosensitizer may have an excitation wavelength of between about 360 nm and about 700 nm, between about 400 nm and about 510 nm, between about 410 nm and about 520 nm, between about 430 nm and about 600 nm, between about 500 nm and about 600 nm, between about 510 nm and about 700 nm, between about 360 nm and about 425 nm, etc. The annihilator may be able to emit photons at a single wavelength, or at more than one wavelength, depending on the annihilator. In some cases, the annihilator may be chosen such that the annihilator has an emission wavelength (or wavelengths) lower than the excitation wavelength of the photosensitizer.

As described herein, the annihilator may be able to transfer energy to another molecule, such as a cleavable moiety or other active moiety, using nonradiative transfer processes such as Forster resonance energy transfer (FRET). Surprisingly, FRET has not previously suggested for transferring energy from one molecule (such as an annihilator) to another molecule (such as an active moiety). Typically in FRET processes, a first molecule, initially in an excited state (e.g., a "donor"), may transfer energy to an acceptor through nonradiative dipole-dipole coupling, which may form part of the cleavable moiety. The efficiency of this energy transfer is usually inversely proportional to the sixth power of the distance between the donor and the acceptor. The energy received by the active moiety can result in cleavage of one or more bonds within or linked to the acceptor, i.e., the acceptor can act as a cleavable moiety, or produce other chemical changes, e.g., photoisomerization, rearrangement, photocycloaddition, or other chemical reactions.

In some exemplary embodiments, the annihilator can be a di-heteroaryl-substituted diketopyrrolopyrrole, such as FDPP, or is TTBP, or analogs thereof. Certain embodiments further comprise a cleavable moiety, which may be a photocleavable moiety able to accept energy from the annihilator.

The formula for FDPP is shown below:

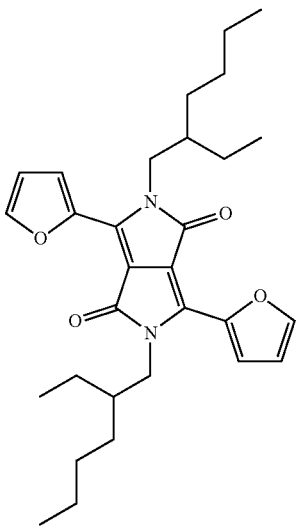 [SMILES: CCCCC(CC)CN1C(=O)C2=C(c3ccco3)N(CC(CC)CCCC)C(=O)C2=C1c1ccco1]

Also intended to be within the scope of the exemplary embodiments described herein are similar diketopyrrolopyrroles, where one or both of the furan rings is replaced with a different heteroaryl ring, such as thiophene, pyrrole, or imidazole, and analogs thereof where one or both of the heteroaryl rings, such as furan, thiophene, pyrrole, or imidazole are substituted with one or two L substituents as described herein.

The formula for TTBP is shown below:

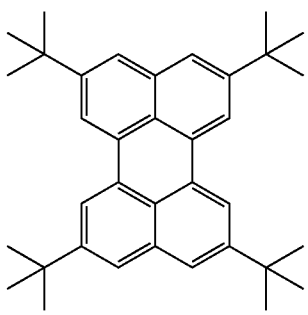 [SMILES: CC(C)(C)c1cc2cc(C(C)(C)C)cc3c4cc(C(C)(C)C)cc5cc(C(C)(C)C)cc(c(c1)c23)c54]

Analogs of TTBP are also intended to be within the scope of the exemplary embodiments described herein. Such analogs include those where one or more of the aryl rings is substituted with one or two L moieties, as defined herein, and/or where one or more of the t-butyl moieties is replaced with a different $C_{3-20}$ branched alkyl moiety, such as a $C_{3-6}$ branched alkyl moiety.

IV. Acceptors

In some embodiments, the acceptor is one or more moiety selected from the group consisting chromophores whose singlet energy is greater than or equal to two times its triplet energy.

In some embodiments, suitable acceptor molecules include polyaromatic hydrocarbons having three or more fused aromatic rings, such as from three to about 20 fused aromatic rings, such as from three to about seven fused aromatic rings. Exemplary general structures for such acceptors are provided below:

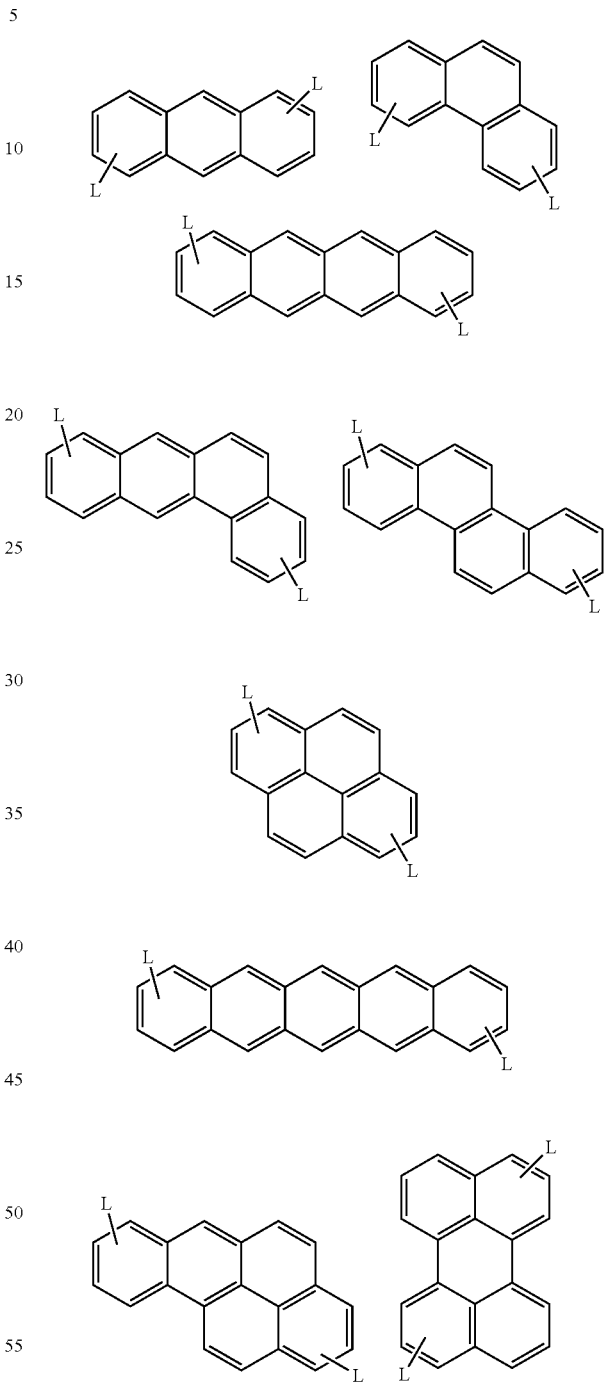

as well as phenanthrene, phenalene, benzo[c]phenanthrene, tetracene, chrysene, tetraphene, pyrene, benzo[a]pyrene, perylene, pentacene, corannulene, benzo[ghi]perylene, coronene, ovalene, among others. Representative tetracenes include tetracenes including cyanation at any position, for example, from 1 to 12 nitrile groups. Individual substituted tetracene compounds include the following compounds, and analogs thereof with from one to three L substituents:

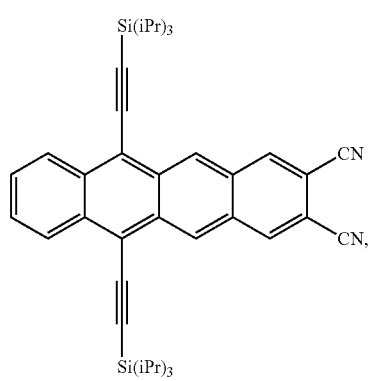

In the structures shown above, L is defined as $C_{1-8}$ alkyl (including cycloalkyl), lower alkenyl ($C_{2-6}$), lower alkynyl ($C_{2-6}$), heterocyclyl, aryl, heteroaryl, arylalkoxycarbonyl, carboxy, halo (e.g., F, Cl, Br, or I), haloalkyl, —OR', —NR'R", hydroxy, hydroxy-$C_{1-6}$ alkyl, alkoxyalkyl($C_{2-8}$), alkoxycarbonyl, —CF$_3$, —CN, —NO$_2$, —C$_2$R', —SR', —N$_3$, —C(=O)NR'R", —NR'C(=O) R", —C(=O)R', —C(=O)OR', —OC(=O)R', —OC(=O)NR'R", —NR'C(=O)OR", —SO$_2$R', —SO$_2$NR'R", —NR'SO$_2$R", N(R')$_2$, SR', OCOR', N(COR')R', N(COR')COR', and SCOR'.

Each R' and R" are, independently, H, a lower alkyl ($C_{1-6}$), lower haloalkyl ($C_{1-6}$), lower alkoxy ($C_{1-6}$), lower alkenyl ($C_{2-6}$), lower alkynyl ($C_{2-6}$), lower cycloalkyl ($C_{3-6}$), aryl, heteroaryl, heterocyclyl, alkylaryl, aryl-$C_{1-6}$-alkyl (such as benzyl); or if two R' reside on the same nitrogen atom they can come together to form an alkyl ring ($C_{3-6}$) containing none or one heteroatom independently selected from N, O, and S; wherein the R' groups can be substituted with one or more substituents as defined above, for example, hydroxyalkyl, aminoalkyl, and alkoxyalkyl.

There can be from 0-3 L moieties per aromatic ring in the structures shown above.

In some exemplary embodiments, rather than being defined as shown above, L represents a covalent bond to an annihilator or to a fluorescent label.

In some exemplary embodiments, suitable acceptor molecules include polyaromatic hydrocarbons having three or more fused aromatic rings, such as from three to about 20 fused aromatic rings, such as from three to about seven fused aromatic rings, and further comprising aromatic substituents having from 6 to about 26 carbon atoms.

In some exemplary embodiments, the acceptor is fluorescent. For example, the acceptor moiety and the annihilator may each be fluorescent entities that are able to interact via FRET.

Non-limiting examples of acceptors include arylcarbonylmethyl groups, 2-nitrobenzyl groups, or coumarin-4-ylmethyl groups. Specific non-limiting examples of coumarin-4-ylmethyl groups include HCM, (7-hydroxycoumarin-4-yl)methyl; MCM, (7-methoxycoumarin-4-yl)methyl; ACM, (7-acetoxycoumarin-4-yl)methyl; PCM, (7-propionyloxycoumarin-4-yl)methyl; DMCM, (6,7-dimethoxycoumarin-4-yl)methyl; BECMEM, (6,7-bis(ethoxycarbonylmethoxy)coumarin-4-yl)methyl; Bhc, (6-bromo-7-hydroxycoumarin-4-yl)methyl; DEACM, (7-diethylaminocoumarin-4-yl)methyl; DMACM, (7-dimethylaminocoumarin-4-yl)methyl, DEAC450, or thiocumarin. In one embodiment, the acceptor is a coumarin derivative. The acceptor may also be a DEACM derivative.

In certain exemplary embodiments, the acceptor has absorption that partially or completely overlaps with the upconversion emission from the annihilator. For example, the acceptor may have an absorption spectrum that includes wavelengths of at least about 360 nm, at least about 370 nm, at least about 380 nm, at least about 390 nm, at least about 400 nm, at least about 410 nm, at least about 420 nm, at least about 430 nm, at least about 440 nm, at least about 450 nm, etc. In some embodiments, the acceptor can have an absorption spectrum of no more than about 700 nm, no more than about 690 nm, no more than about 680 nm, no more than about 670 nm, no more than about 660 nm, no more than about 650 nm, no more than about 640 nm, no more than about 630 nm, no more than about 620 nm, no more than about 610 nm, no more than about 600 nm, etc. Combinations of any of these wavelengths are also possible; as non-limiting examples, the absorption may be between about 360 nm and about 700 nm, between about 400 nm and about 510 nm, between about 410 nm and about 520 nm, between about 430 nm and about 600 nm, between about 500 nm and about 600 nm, between about 510 nm and about 700 nm, between about 360 nm and about 425 nm, etc.

In some exemplary embodiments, the acceptor (which may be contained within an active moiety such as a cleavable moiety) may be positioned such that FRET may be used to transfer energy nonradiatively between the annihilator and the acceptor. For example, the annihilator and the acceptor may be directly covalently bound to each other, or indirectly immobilized to each other, e.g., through covalent binding to one or more linking entities between the annihilator and the active moiety. However, in some cases, the annihilator and the acceptor may be physically positioned within close proximity to each other. For instance, the annihilator and the acceptor can be contained within a carrier material, for example, contained within a liposome, a polymer film, a particle, a micelle, or the like. In some cases, the annihilator and the acceptor can be positioned such that they are separated by a distance of less than about 15 nm, less than about 13 nm, less than about 12 nm, less than about 11 nm, less than about 10 nm, less than about 9 nm, less than about 8 nm, less than about 7 nm, less than about 6 nm, less than about 5 nm, less than about 4 nm, less than about 3 nm, less than about 2 nm, or less than about 1 nm from each other.

In some exemplary cases, the transfer of energy to the acceptor results in the cleavage of a bond within or linked to the acceptor, and/or within or linked to a different portion of a cleavable moiety containing the acceptor. Cleavage of the bond, in some embodiments, can cause the release of a portion of the cleavable moiety, e.g., as a releasable moiety. However, it should be understood that in other embodiments, the cleavage of a single bond does not necessarily require the release of a releasable moiety, for instance, if more than one bond connects portions of the molecule together. In addition, in some embodiments, transfer of energy to acceptor may result in other chemical reactions within the acceptor, not necessarily leading to the cleavage of a cleavable bond.

If present, a releasable moiety may be any suitable moiety that can be released, e.g., during cleavage (including photocleavage). The releasable moiety can include the acceptor, and/or a portion of the cleavable entity that is separate from the acceptor, but is cleaved as a result of the transfer of energy to the acceptor, e.g., via FRET. Different releasable moieties can be used in various embodiments, depending on the application. For example, the releasable moiety may include a drug, a tracer (e.g., a fluorescent or radioactive compound), a caged species, a peptide or protein, a small molecule (e.g., having a molecular weight of less than about 1 kDa or about 2 kDa), or the like. In some cases, the exact form of the releasable moiety is not critical, e.g., if it is attached through a cleavable bond of a cleavable moiety that itself is cleaved as discussed above; cleavage of the cleavable bond may thereby cause separation of the releasable moiety, regardless of the exact composition of the releasable moiety.

As non-limiting examples, in one set of exemplary embodiments, the releasable moiety can include an anti-angiogenesis drug, such as TNP-470 or Combretastatin A4. In another set of embodiments, the releasable moiety may include an anti-inflammatory drug, such as dexamethasone. In yet another set of embodiments, the releasable moiety includes an anticancer drug and/or a chemotherapy drug, such as doxorubicin, topotecan, or verteporfin. In yet another set of embodiments, the releasable moiety may include fluorescent proteins, such as GFP or YFP. In still another set of embodiments, the releasable moiety can include fluorescent compounds, such as fluorescein, rhodamine, or calcein. In still another set of embodiments, the releasable moiety includes a peptide or a protein, such as an RGD peptide. In another set of embodiments, the releasable moiety may include a radioactive atom, such as $^{3}$H, $^{11}$C, $^{13}$N, $^{14}$C, $^{15}$O, $^{18}$F, $^{24}$Na, $^{32}$P, $^{33}$P, $^{35}$S, $^{36}$Cl, $^{46}$Sc, $^{56}$Mn, $^{60}$Co, $^{89}$Sr, $^{90}$Y, $^{99m}$Tc, $^{103}$Pd, $^{106}$Ru, $^{123}$I, $^{125}$I, $^{129}$I, $^{131}$I, $^{137}$I, $^{137}$Cs, $^{153}$Sm, $^{177}$Lu, or $^{192}$Ir.

However, in other exemplary embodiments, the transfer of energy to the acceptor results in other changes within an active moiety. For instance, the transfer of energy may result in photoisomerization (e.g., of azobenzene-based, azotolane-based, spiropyran-based, or fulvalene diruthenium (FvRu2) molecules), photo-induced Wolff rearrangement (e.g., of 2-diazo-1,2-naphthoquinone (DNQ) groups), or photocycloaddition (e.g., of [2+2] photocyclo addition of coumarin groups, e.g., coumarin groups such as those discussed herein). In another embodiment, the transfer of energy may be used to produce OH radical groups (.OH) or water splitting, e.g., using DPA/PdOEP systems.

V. Carrier Materials

In some exemplary embodiments, the photosensitizer, the annihilator, the active moiety (e.g., a cleavable moiety), and/or the releasable moiety (if present) are contained within a suitable carrier material. The carrier material may hold some or all of these in close proximity to each other (e.g., as discussed above). In some cases, the carrier material may create an environment favorable for compounds such as those discussed herein to be fluorescent and/or to be able to absorb electrons, photons, etc. as described herein. For example, the carrier material may create an aqueous environment, a hydrophobic environment, a polar or non-polar environment, etc. In some cases, the carrier material creates an environment that repels water.

In one set of exemplary embodiments, the carrier material is formed from a polymer. Any suitable polymer can be used. Examples of polymers include, but are not limited to, polylactic acid, polyglycolic acid, polyethylene oxide, polystyrene, polyethylene, polypropylene, etc. In some embodiments, the polymer may be biodegradable or biocompatible, e.g., for use in various medical or biological applications. In some cases, more than one polymer can be used, and the polymers may be physically blended together and/or chemically combined, e.g., as in a copolymer. As a non-limiting example, the carrier material may include a copolymer such as poly(D,L-lactic acid)-poly(ethylene oxide).

However, it should be understood that the carrier material need not be limited to polymeric materials. For example, in other embodiments, the carrier material can include silica, ceramics, or other materials.

The carrier material can be present in any suitable form. For example, the carrier material can be present as a film, as a block of material, as particles, as a micelle, or the like. In some cases, components such as the photosensitizer, the annihilator, the active moiety, and/or the releasable moiety may be added to the carrier material during and/or after formation of the carrier material. The carrier material can be formed using any suitable techniques; for example, techniques for producing polymers, silica gels, ceramics, etc, are known to those of ordinary skill in the art.

If the carrier material is present as particles, the particles may be spherical or nonspherical, and may have any suitable diameter. For instance, the particles may have an average diameter of less than about 1 mm, less than about 500 micrometers, less than about 300 micrometers, less than about 100 micrometers, less than about 50 micrometers, less than about 30 micrometers, less than about 10 micrometers, less than about 5 micrometers, less than about 3 micrometers, less than about 1 micrometer, less than about 500 nm, less than about 300 nm, less than about 100 nm, less than about 50 nm, less than about 30 nm, less than about 10 nm, etc. The average diameter of a nonspherical particle may be taken as the volume of a perfect sphere having the same volume of the particle.

If the carrier material is present as a film, the film can have any cross-sectional thickness. For example, the film may have an average thickness of less than about 1 mm, less than about 500 micrometers, less than about 300 micrometers, less than about 100 micrometers, less than about 50 micrometers, less than about 30 micrometers, less than about 10 micrometers, less than about 5 micrometers, less than about 3 micrometers, less than about 1 micrometer, less than about 500 nm, less than about 300 nm, less than about 100 nm, less than about 50 nm, less than about 30 nm, less than about 10 nm, etc.

The carrier material may also comprise one or more polymeric micelles. The polymer micelles may have any suitable average diameter. For example, the micelles can have an average diameter of less than about 1 mm, less than about 500 micrometers, less than about 300 micrometers, less than about 100 micrometers, less than about 50 micrometers, less than about 30 micrometers, less than about 10 micrometers, less than about 5 micrometers, less than about 3 micrometers, less than about 1 micrometer, less than about 500 nm, less than about 300 nm, less than about 100 nm, less than about 50 nm, less than about 30 nm, less than about 10 nm, etc.

VI. Exemplary Methods of Use

As described herein, exemplary compositions such as those discussed herein may be used in a wide variety of applications, including biological and medical applications, as well as non-biological or non-medical applications. As a non-limiting example, in one set of embodiments, a composition as discussed herein may be applied to a subject. The subject may be human or non-human. For example, the subject may be a rat, mouse, rabbit, goat, cat, dog, or the like. The composition can also be applied to any suitable sample, e.g., a biological sample, a physical sample, a chemical sample, or the like.

Light may be applied to the composition to cause release of the releasable moiety, if present. The light may be monochromatic light (e.g., laser or coherent light), or the light may be nonmonochromatic or noncoherent in some embodiments. The light may have any suitable frequency, e.g., including the frequencies discussed herein. In some cases, the light has a frequency such that the average energy of the incident light is insufficient to cause direct cleavage of the cleavable moiety or interact with an active moiety, but due to upconversion, etc., as discussed herein, the incident light may cause cleavage of the cleavable moiety, photoreaction within the active moiety, or release of the releasable moiety, etc.

In one set of exemplary embodiments, the light is applied at an irradiance of at least about 1 $mW/cm^2$, at least about 2 $mW/cm^2$, at least about 5 $mW/cm^2$, at least about 10 $mW/cm^2$, at least about 20 $mW/cm^2$, at least about 30 $mW/cm^2$, at least about 40 $mW/cm^2$, at least about 50 $mW/cm^2$, at least about 60 $mW/cm^2$, at least about 70 $mW/cm^2$, at least about 80 $mW/cm^2$, at least about 90 $mW/cm^2$, at least about 100 $mW/cm^2$, at least about 110 $mW/cm^2$, at least about 125 $mW/cm^2$, at least about 150 $mW/cm^2$, at least about 200 $mW/cm^2$, at least about 250 $mW/cm^2$, at least about 300 $mW/cm^2$, at least about 400 $mW/cm^2$, at least about 500 $mW/cm^2$, etc. In some cases, the light is applied at an irradiance of no more than about 1000 $mW/cm^2$, no more than about 500 $mW/cm^2$, no more than about 400 $mW/cm^2$, no more than about 300 $mW/cm^2$, no more than about 250 $mW/cm^2$, no more than about 200 $mW/cm^2$, no more than about 150 $mW/cm^2$, no more than about 125 $mW/cm^2$, no more than about 110 $mW/cm^2$, no more than about 100 $mW/cm^2$, no more than about 90 $mW/cm^2$, no more than about 80 $mW/cm^2$, no more than about 70 $mW/cm^2$, no more than about 60 $mW/cm^2$, no more than about 50 $mW/cm^2$, no more than about 40 $mW/cm^2$, no more than about 30 $mW/cm^2$, no more than about 20 $mW/cm^2$, no more than about 10 $mW/cm^2$, no more than about 5 $mW/cm^2$, no more than about 2 $mW/cm^2$, etc. Combinations of any of the above are also possible in certain embodiments. For instance, the light may be applied at an irradiance of between about 50 $mW/cm^2$ and about 150 $mW/cm^2$.

In one set of exemplary embodiments, the composition can be applied to a subject to treat a tumor.

The composition may be applied directly to the tumor, and/or applied systemically to the body of the subject such that at least some of the composition is able to travel to the tumor (e.g., via the blood) such that light can be applied to the tumor (or portion thereof), e.g., to cause release of a releasable moiety for determining and/or treating the tumor. The composition can include, for example, an anti-angiogenesis drug, an anti-inflammatory drug, a radioactive species, an anticancer drug and/or a chemotherapy drug, and light may be applied to the tumor to cause release. Such application may be targeted, e.g., by applying light directly to the tumor (or at least a portion thereof); thus, release elsewhere within the subject may be minimized by not applying light to other places. In such a fashion, release of a drug (or other suitable release moiety) may be controlled or localized at or near the tumor by applying light directly to the tumor (or portion thereof), or at least proximate the tumor. In some cases, more than one composition may be present.

In another set of exemplary embodiments, the composition may be applied to a subject for treatment to the eye. The eye is sensitive to light, and in fact, too much light may be harmful to the eye. Thus, by using compositions such as those described herein, in some cases, light intensities or irradiation to the eye can be minimized while still being able to cause cleavage of a cleavable moiety, reaction within an active moiety, and/or release of a releasable moiety. The subject may, for example, have various eye conditions in need of treatment, such as macular degeneration (e.g., age-related macular degeneration) or retinoblastoma. The composition can be applied directly to the eye, and/or applied systemically to the body such that at least some of the composition is able to travel to the eye (e.g., via the blood) such that light can be applied to the eye (or a portion of the eye) to interact with the composition as discussed herein. One or both eyes may be treated, depending on the condition of the subject.

Other portions of a subject may also be treated in various embodiments. For instance, the composition may be applied directly to a specific location within the subject, or applied systemically to the subject such that at least some of the composition is able to travel to a location where light is to be applied. For instance, the composition may be applied to the skin (or to the blood) and light applied to a portion of the skin to cause local release of a releasable moiety.

VII. Exemplary Pharmaceutical Compositions

In various exemplary aspects, the compositions described herein can be administered by any suitable method, e.g., contained in a solution or suspension, such as inhalation solutions, local installations, eye drops, intranasal introductions, an ointment for epicutaneous applications, intravenous solutions, injection solutions (e.g., subcutaneous, or intravenous), or suppositories. In one set of embodiments, the composition is introduced parenterally or topically. For instance, the composition may be contained within a cream, gel, or ointment applied to the skin. In some embodiments, the composition can be applied one or more times a day, by one or more administrations per day, by fewer than one time per day, or by continuous administration, etc., until a desired therapeutic effect is achieved.

In some exemplary embodiments, the composition is introduced to the subject at a dose from, e.g., 0.01 to 100.0 mg of the composition per kg of body weight of the subject. In some cases, the dose may be at least about 0.01 mg/kg, at least about 0.03 mg/kg, at least about 0.05 mg/kg, at least about 0.1 mg/kg, at least about 0.3 mg/kg, at least about 0.5 mg/kg, at least about 1 mg/kg, at least about 3 mg/kg, at least about 5 mg/kg, at least about 10 mg/kg, at least about 30 mg/kg, at least about 50 mg/kg, and/or no more than about 100 mg/kg, no more than about 50 mg/kg, no more than about 30 mg/kg, no more than about 10 mg/kg, no more than about 5 mg/kg, no more than about 3 mg/kg, no more than about 1 mg/kg, no more than about 0.5 mg/kg, no more than about 0.3 mg/kg, no more than about 0.1 mg/kg, no more than about 0.05 mg/kg, no more than about 0.03 mg/kg, etc. Where the composition is administered as a solution, the solution may have, for example, a concentration of between about 1% to about 10% of the composition. In one set of embodiments, the composition may be, or include, a pharmaceutically acceptable derivative, e.g., for parenteral use is in a pharmaceutically acceptable solvent such as, for example, an aqueous solution including water, glucose solution, isotonic solutions of sodium chloride, buffered salt solutions, or the like. Other physiological solvents or carriers can be used in other exemplary embodiments.

As described herein, certain aspects of the exemplary embodiments of the present disclosure can provide methods of administering any composition of the present disclosure to a subject. When administered, the compositions of the present disclosure are applied in a therapeutically effective, pharmaceutically acceptable amount as a pharmaceutically acceptable formulation. As used herein, the term "pharmaceutically acceptable" is given its ordinary meaning. Pharmaceutically acceptable compositions are generally compatible with other materials of the formulation and are not generally deleterious to the subject. Any of the compositions of the exemplary embodiments of the present disclosure may be administered to the subject in a therapeutically effective dose. A "therapeutically effective" amount as used herein means that amount necessary to delay the onset of, inhibit the progression of, halt altogether the onset or progression of, diagnose a particular condition being treated, or otherwise achieve a medically desirable result. When administered to a subject, effective amounts will depend on the particular condition being treated and the desired outcome. A therapeutically effective dose may be determined by those of ordinary skill in the art, for instance, employing factors such as those further described below and using no more than routine experimentation.

Any medically acceptable method may be used to administer the composition to the subject. The administration may be localized (i.e., to a particular region, physiological system, tissue, organ, or cell type) or systemic, depending on the condition to be treated. For example, the composition may be administered orally, vaginally, rectally, buccally, pulmonary, topically, nasally, transdermally, through parenteral injection or implantation, via surgical administration, or any other method of administration. Examples of parenteral modalities that can be used with the present disclosure include intravenous, intradermal, subcutaneous, intracavity, intramuscular, intraperitoneal, epidural, or intrathecal. Examples of implantation modalities include any implantable or injectable drug delivery system. Use of an implant may be particularly suitable in some embodiments of the present disclosure. The implant containing the composition may be constructed and arranged to remain within the body for at least 30 or 45 days, and preferably at least 60 or 90 days, or even longer in some cases. Long-term release implants are well known to those of ordinary skill in the art.

In certain exemplary embodiments of the present disclosure, a composition can be combined with a suitable pharmaceutically acceptable carrier, for example, as incorporated into a liposome, incorporated into a polymer release system, or suspended in a liquid, e.g., in a dissolved form, or a colloidal form, or a micellular form. In general, pharmaceutically acceptable carriers suitable for use in the present disclosure are well-known to those of ordinary skill in the art. A pharmaceutically acceptable carrier may include non-toxic material that does not significantly interfere with the effectiveness of the biological activity of the active compound(s) to be administered, but is used as a formulation ingredient, for example, to stabilize or protect the active compound(s) within the composition before use. The carrier may be organic or inorganic, and may be natural or synthetic, with which one or more active compounds of the present disclosure are combined to facilitate the application of the composition. The carrier may be either soluble or insoluble, depending on the application. Examples of well-known carriers include glass, polystyrene, polypropylene, polyethylene, dextran, nylon, amylase, natural and modified cellulose, polyacrylamide, agarose and magnetite. The nature of the carrier can be either soluble or insoluble. Those skilled in the art will know of other suitable carriers, or will be able to ascertain such, using only routine experimentation.

In some exemplary embodiments, the compositions of the present disclosure include pharmaceutically acceptable carriers with formulation ingredients such as salts, carriers, buffering agents, emulsifiers, diluents, excipients, chelating agents, fillers, drying agents, antioxidants, antimicrobials, preservatives, binding agents, bulking agents, silicas, solubilizers, or stabilizers that may be used with the active compound. For example, if the formulation is a liquid, the carrier may be a solvent, partial solvent, or non-solvent, and may be aqueous or organically based. Examples of suitable formulation ingredients include diluents such as calcium carbonate, sodium carbonate, lactose, kaolin, calcium phosphate, or sodium phosphate; granulating and disintegrating agents such as corn starch or algenic acid; binding agents such as starch, gelatin or acacia; lubricating agents such as magnesium stearate, stearic acid, or talc; time-delay materials such as glycerol monostearate or glycerol distearate; suspending agents such as sodium carboxymethylcellulose, methylcellulose, hydroxypropylmethylcellulose, sodium alginate, polyvinylpyrrolidone; dispersing or wetting agents such as lecithin or other naturally-occurring phosphatides; thickening agents such as cetyl alcohol or beeswax; buffering agents such as acetic acid and salts thereof, citric acid and salts thereof, boric acid and salts thereof, or phosphoric acid and salts thereof; or preservatives such as benzalkonium chloride, chlorobutanol, parabens, or thimerosal.

Suitable carrier concentrations can be determined by those of ordinary skill in the art, using no more than routine experimentation. The compositions of the present disclosure may be formulated into preparations in solid, semi-solid, liquid or gaseous forms such as tablets, capsules, elixirs, powders, granules, ointments, creams, gels, pastes, solutions, depositories, inhalants, injectables, or the like. Those of ordinary skill in the art will know of other suitable formulation ingredients, or will be able to ascertain such, using only routine experimentation.

VIII. Exemplary Kits

In another exemplary aspect, the present disclosure is directed to a kit including one or more of the compositions discussed herein. A "kit," as used herein, typically defines a package or an assembly including one or more of the compositions of the present disclosure, and/or other compositions associated with the present disclosure, for example, as described herein. Each of the compositions of the kit may be provided in liquid form (e.g., in solution), or in solid form (e.g., a dried powder). In certain cases, some of the compositions may be constitutable or otherwise processable (e.g., to an active form), for example, by the addition of a suitable solvent or other species, which may or may not be provided with the kit. Examples of other compositions or components associated with the present disclosure include, but are not limited to, solvents, surfactants, diluents, salts, buffers, chelating agents, fillers, antioxidants, binding agents, bulking agents, preservatives, drying agents, antimicrobials, needles, syringes, packaging materials, tubes, bottles, flasks, beakers, dishes, frits, filters, rings, clamps, wraps, patches, containers, and the like, for example, for using, administering, modifying, assembling, storing, packaging, preparing, mixing, diluting, and/or preserving the compositions components for a particular use, for example, to a sample and/or a subject.

A kit of the exemplary embodiments of the present disclosure may, in some cases, include instructions in any form that are provided in connection with the compositions of the present disclosure in such a manner that one of ordinary skill in the art would recognize that the instructions are to be associated with the compositions of the present disclosure. For instance, the instructions may include instructions for the use, modification, mixing, diluting, preserving, administering, assembly, storage, packaging, and/or preparation of the composition and/or other compositions associated with the kit. In some cases, the instructions may also include instructions for the delivery and/or administration of the compositions, for example, for a particular use, e.g., to a sample and/or a subject. The instructions may be provided in any form recognizable by one of ordinary skill in the art as a suitable vehicle for containing such instructions, for example, written or published, verbal, audible (e.g., telephonic), digital, optical, visual (e.g., videotape, DVD, etc.) or electronic communications (including Internet or web-based communications), provided in any manner.

EXAMPLES

The following Examples of the exemplary embodiments of the present disclosure are provided only to further illustrate the present disclosure, and are not intended to limit its scope.

Example 1

Triplet-triplet annihilation (TTA) is an upconversion process which can be driven by low-power noncoherent light sources, which enhances safety and is of practical and economic benefit. In TTA-upconversion, a low-energy photon is absorbed by a photosensitizer, which then undergoes intersystem crossing (ISC) to form a more stable triplet state. The triplet state energy of the photosensitizer is subsequently transferred to a molecule which is thus excited to its triplet state. Two such molecules in the triplet state can then combine their energies through TTA to form one molecule in the singlet state (with higher energy), and another in the ground state. (Those molecules are often termed annihilators because their interaction "annihilates" the triplet state.) The molecule in the singlet state can relax to the ground state, usually by emission of a higher-energy photon.

Relaxation to the ground state can also be achieved by Forster resonance energy transfer (FRET). TTA-UC is coupled with FRET to create an upconversion-based photoresponsive nanoparticulate system. Incident long-wavelength light is efficiently upconverted to high energy through TTA, and transferred by FRET to a photocleavable group, triggering its cleavage; some of the energy may also go to emitting one or more photons. Cleavage of that bond removes the photocleavable (caging) group from a targeting ligand, restoring its binding activity.

This exemplary embodiment uses PdPc(OBu)$_8$ as a photosensitizer and FDPP as the annihilator in a composition for triplet upconversion, due to their unexpected high upconversion efficiency. One of ordinary skill will understand that other molecules of the same class as FDPP (diketopyrrolopyrroles) can be used. One of ordinary skill will understand how to combine the photosentizer and annihilator with other components of a composition, such as a carrier material, cleavage moiety or releasable moiety. Representative examples of reactions driven by near infrared (NIR) light are provided below:

a Hydrodehalogenation

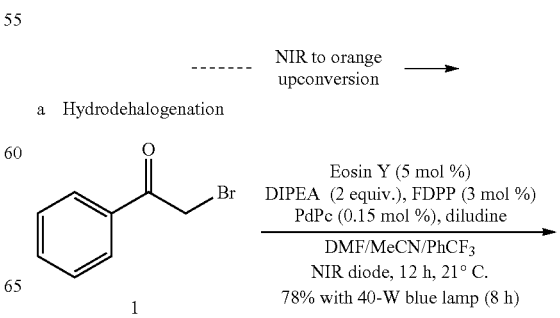

-continued
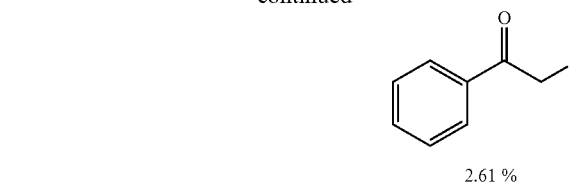
2.61 %
b  Oxidation
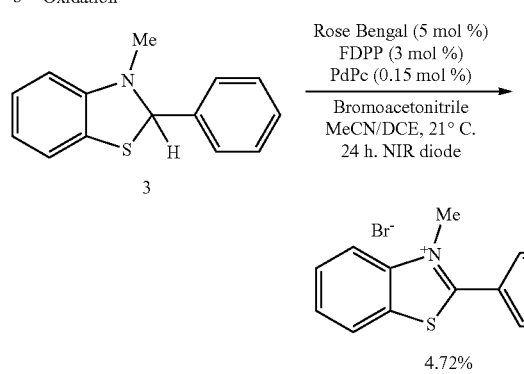
c  Radical cyclization
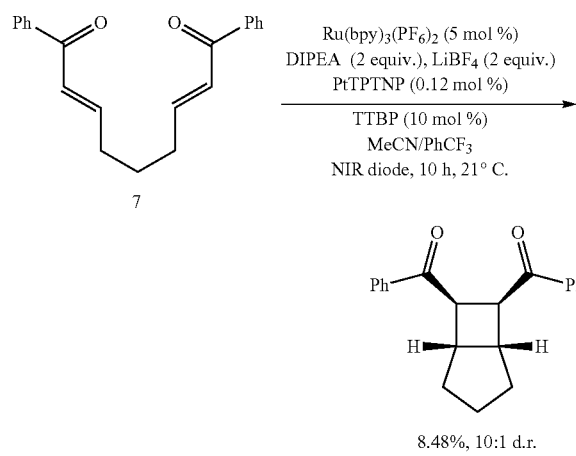
e  Vinyl azide sensitization
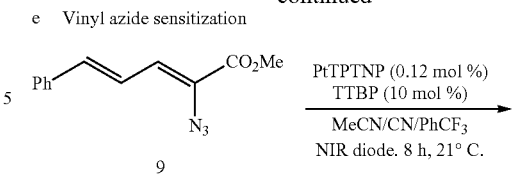
f  Radical polymerization
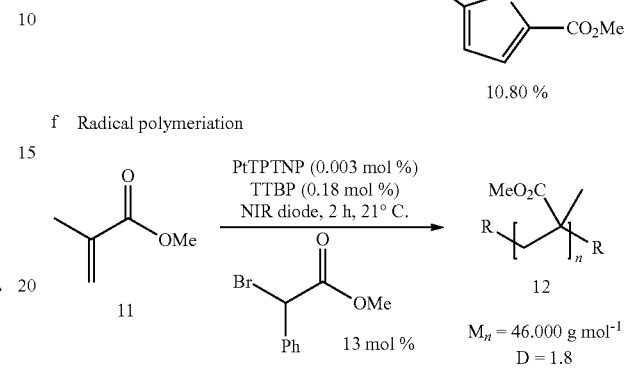
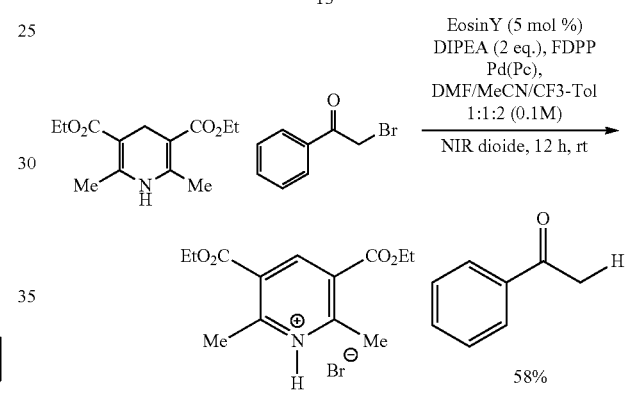
Neumann, Matthias; Idner, Stefan F.; König, Burkhard; Zeitler, Kirsten. *Angew. Chem. Int. Ed* 2011, 50, 951-954.
Control Reactions:
no Eosin Y: 3%
no DIPEA: 9%
no FDPP: 3%
no Pd(Pc): 2%
no NIR: 3%
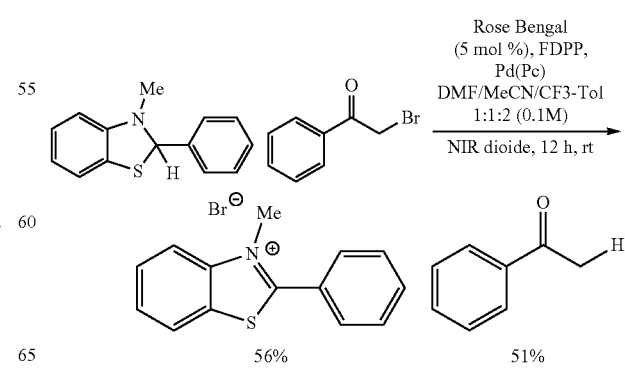

Mashraqui, Sablr H.; Kellogg, Richard M. *Tetrahedron Letters* 1985, 26, 1453-1456.

Control Reactions: (% acetophenone)

no RB: 4% no FDPP: 1% no Pd(Pc): 2% no NIR: 2%

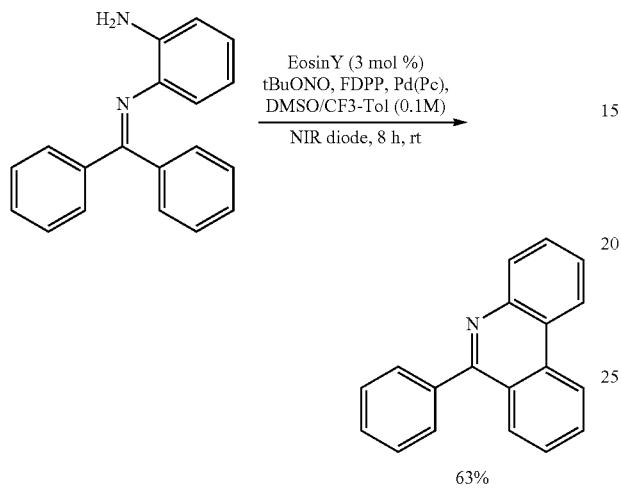

63%

Natarajan, Palani; Kumar, Naveen; Sharma, Manjeet. *Org. Chem. Front.* 2016, 3, 1265-1270.

Control Reactions:

no Eosin Y: 3% no FDPP: 2% no Pd(Pc): 2% no NIR: 3%

Example 2

This exemplary embodiment uses PtTPTNP as a photosensitizer and TTBP as the annihilator in a composition for triplet upconversion, due to their unexpected high upconversion efficiency. One of ordinary skill will understand how to combine the photosentizer and annihilator with other components of a composition, such as a carrier material, cleavage moiety or releasable moiety.

Example 3

Figure 4:
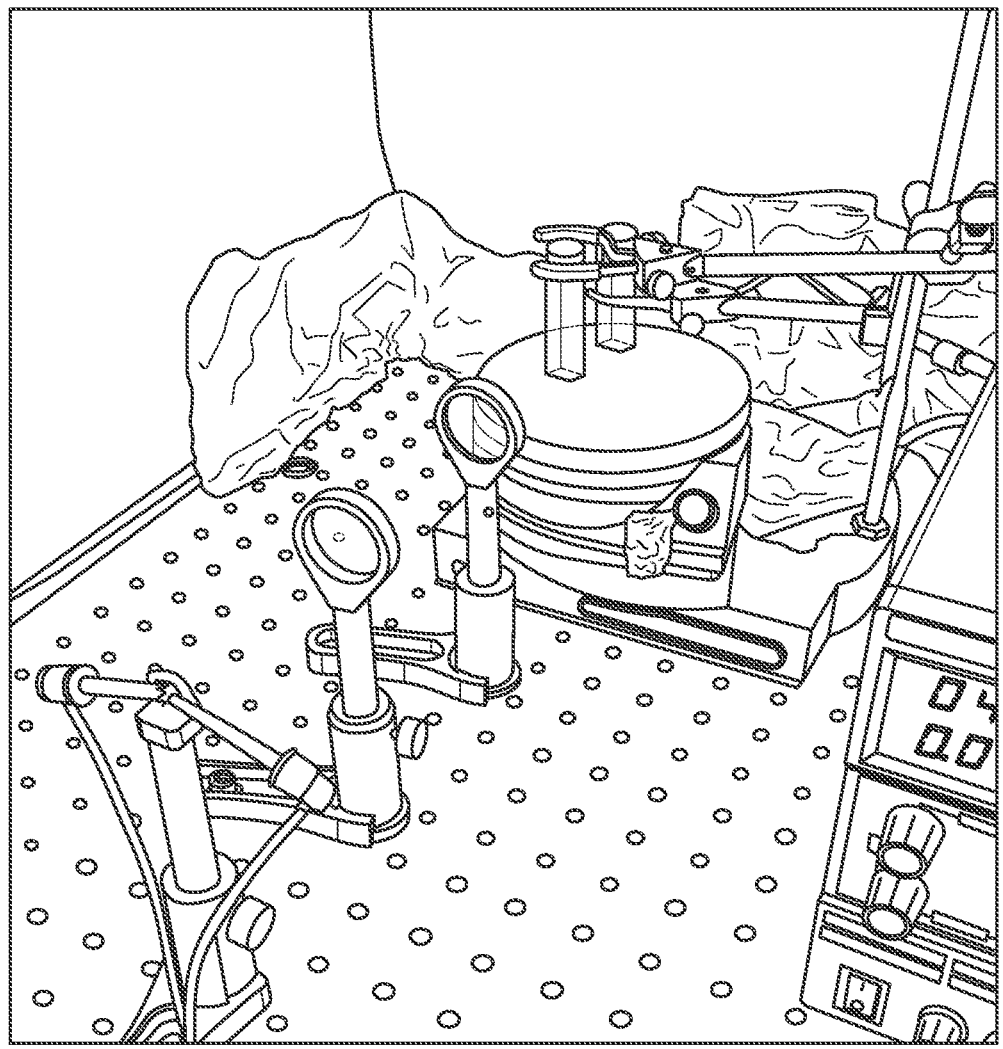
FIG. 4 is a photograph which shows the chemical reaction to form a crosslinked PMMA gel, using MMA monomer with 5% ethylene glycol dimethacrylate as a crosslinker to create a freestanding gel, while using visible light-absorbing materials to disrupt the path of the incident laser.

To demonstrate the ability of NIR light (730 nm), versus blue light (450 nm), to penetrate a range of media, we performed the MMA polymerization with 5% ethylene glycol dimethacrylate as a crosslinker to generate a freestanding gel, while using several visible-light-absorbing materials to disrupt the path of the incident laser (FIG. 4). Reactions that bypass the barrier create a gel.

A PMMA gel was synthesized with an NIR light source through various different barriers; meanwhile, a gel was not formed when the 450-nm blue light source was used, presumably owing to its limited penetrating ability. The chemical reaction, and corresponding results, are tabulated below.

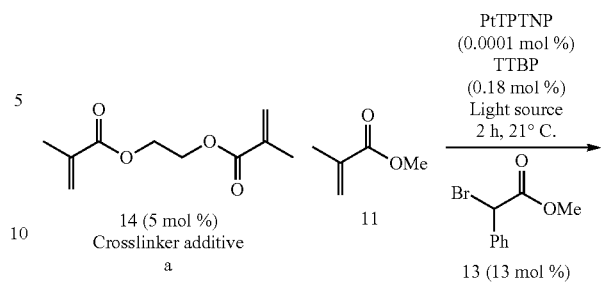

| Material | NIR | Blue |
|---|---|---|
| Air | Gel | Gel |
| Water | Gel | Gel |
| Amber glass | Gel | No reaction |
| Bacon | Gel | No reaction |
| Ru(bpy)3(PF6)2 (1.5 mM) | Gel | No reaction |
| 700-nm long-pass filter | Gel | No reaction |
| White silicone sheet | Gel | No reaction |
| 3 sheets white paper | Gel | No reaction |
| Hemoglobin (0.2 mM) | Gel | No reaction |
| Pig skin (6.4 mm) | Gel | No reaction |

*Experiment halted after 15 minutes owing to fire hazard, as the bacon began to burn upon irradiation.

Figure 5:
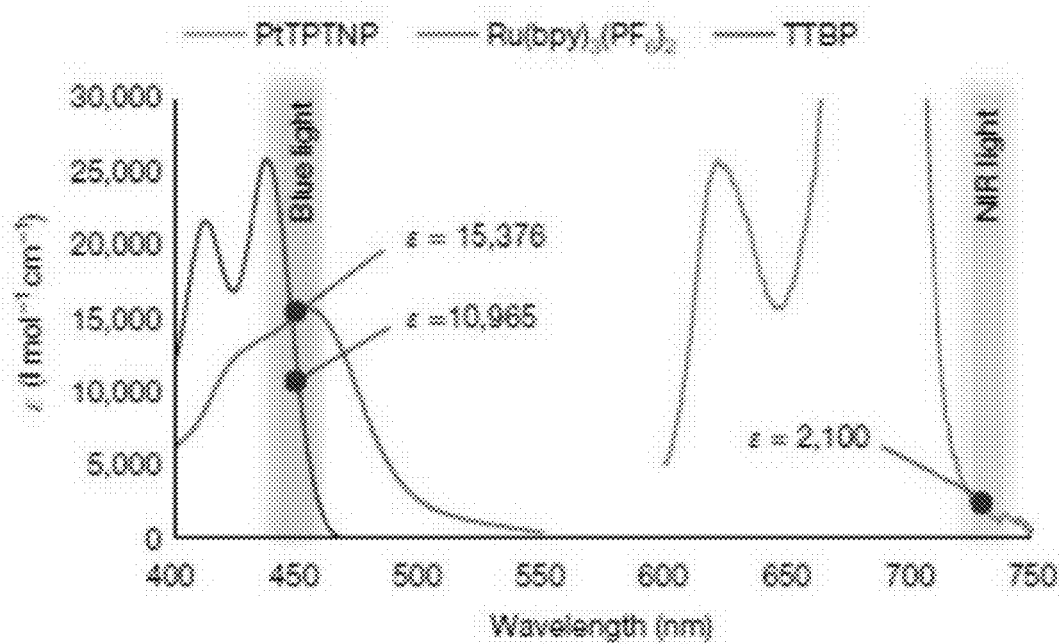
FIG. 5 is a chart showing the application of Beer-Lambert law to blue and NIR light, shown in terms of epsilon ($\varepsilon$, 1 mol$^{-1}$ cm$^{-1}$) and wavelength (nm).

Notably, the NIR light showed excellent penetrating power through hemoglobin, a component of human blood that absorbs visible light. In addition to the gelation reaction, the [2+2] cyclization reaction shown above was performed through a barrier of 0.2 mM hemoglobin solution. The product yield with the NIR laser was 46%—identical to that of the reaction conducted without a barrier—whereas the blue laser gave a 1% yield. The scale-up of visible-light photoredox reactions suffers from shallow light absorption, as evidenced by slow reaction rates. In addition, increasing the size of the reaction vessel decreases the relative surface area, thus reducing photon exposure and fundamentally limiting photocatalyst excitation. Infrared photoredox can overcome both of these challenges. For example, the penetration of infrared light through the [2+2] cyclization reaction mixture is 304 times deeper than that of blue light, based on concentration and extinction coefficients (FIG. 5). As shown in FIG. 5, comparison of extinction coefficients and concentrations of Ru(bpy)$_3$(PF$_6$)$_2$ and TTBP with those of PtTPTNP reveals a large increase in reaction penetration by infrared light compared to blue light, according to the Beer-Lambert relation A=$\epsilon$cl (A, absorbance; $\epsilon$, molar extinction coefficient; c, concentration; l, path length). For [Ru(bpy)$_3$]$^{2+}$, $\epsilon$ was 7.29 times larger and c was 41.7 times larger than for PtTPTNP; infrared light (730 nm) thus penetrated 304 times further than blue light (450 nm) through the reaction solution in the 2+2 cyclization reaction shown above. For TTBP, $\epsilon$ was 5.17 times larger and c was 56.7 times larger than for PtTPTNP; the penetration of infrared light (730 nm) was therefore 293 times greater than that of blue light (450 nm) through the reaction solution in the radical polymerization reaction shown above.

Figure 6A:
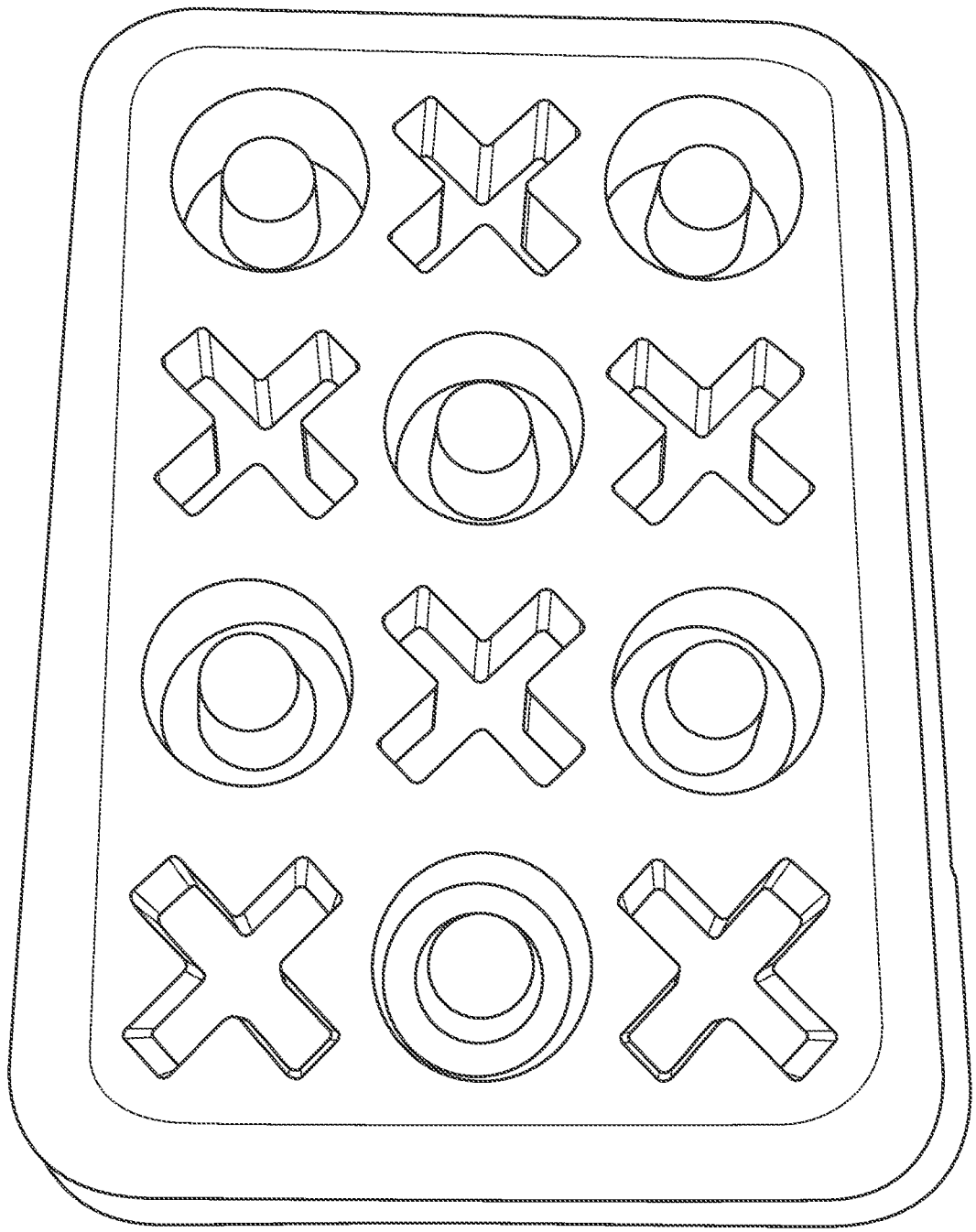
FIG. 6A is a photograph of an opaque silicone mold in which polymerization of MMA to form PMMA was performed.
Figure 6B:
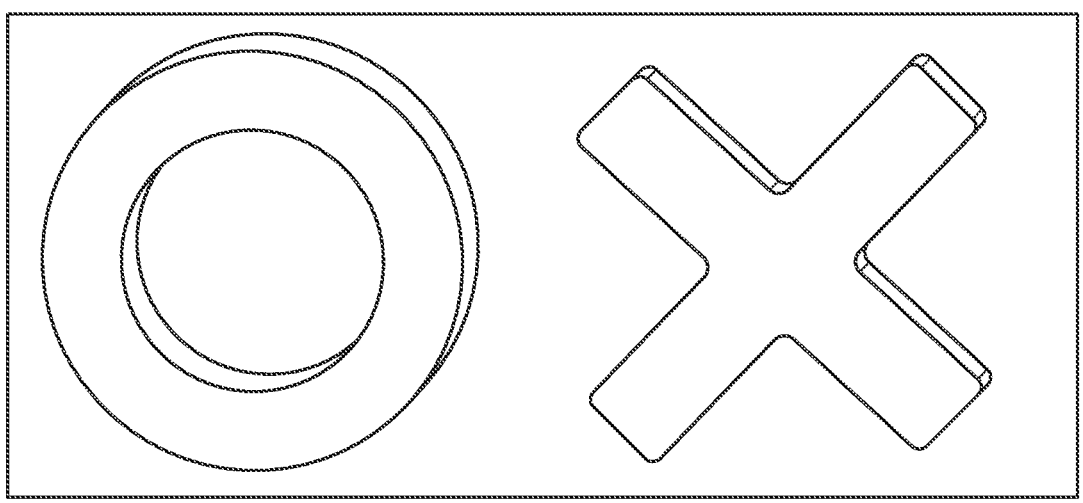
FIG. 6B is a photograph showing the resulting PMMA polymer shapes formed when MMA was polymerized in the opaque silicone mold.

By the same analysis, infrared light penetrated 293 times further than blue light through the free radical polymerization reaction mixture shown above, thus rendering this chemistry scalable. This reaction also demonstrated that a laser is not necessary to perform upconversion, suggesting that this technique can be broadly applied. Scalability and improved penetration through materials were demonstrated by performing polymerization on a multi-gram scale in an opaque silicone mold (FIG. 6A shows the mold, and FIG. 6B shows the resulting PMMA polymer shapes). The sealed mold is resistant to visible light, while the NIR photons pass through uninhibited. The defined shapes were achieved only with the NIR lamp and not with the blue lamp. Using this approach, one can observe the effects of the penetration of infrared radiation through various barriers.

Example 4

Figure 3D:
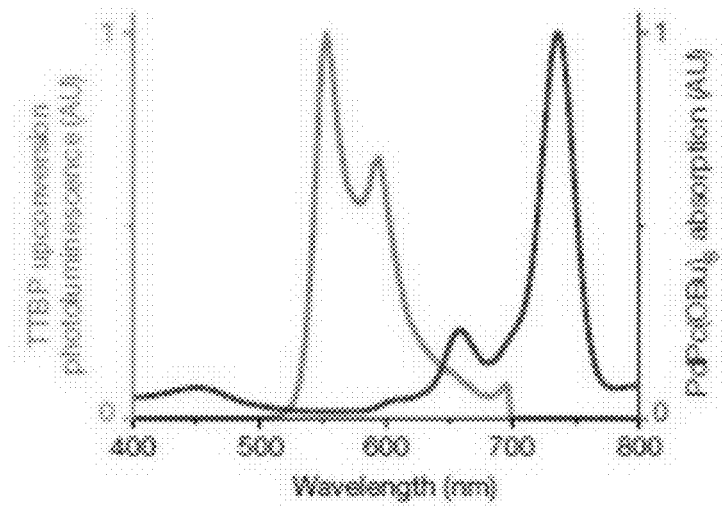
FIG. 3D is an exemplary graph showing NIR-to-orange upconversion photoluminescence using FDPP and PdPc (OBu)$_8$.
Figure 3E:
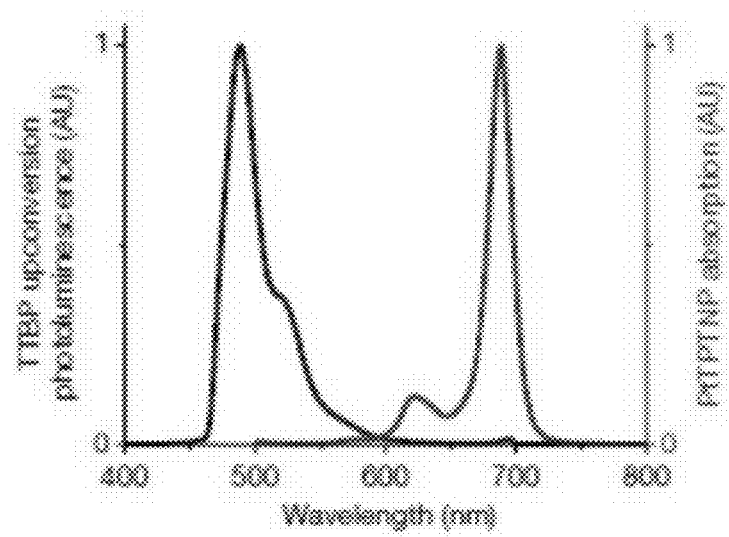
FIG. 3E is an exemplary graph showing NIR-to-blue upconversion photoluminescence using TTBP and PtTPTNP.

An exemplary graph of a normalized upconversion photoluminescence (UCPL) of a degassed solution of $4\times10^{-3}$M FDPP and $5\times10^{-5}$M PdPc(OBu)$_8$ in toluene is shown in FIG. 3C. in darker shade, with a 700 nm shortpass filter on the detector. The normalized absorbance spectra of PdPc(OBu)$_8$ is shown in lighter shade, whereas the sample was irradiated with a 90 mA 730 nm laser diode, is shown in a darker shade. An exemplary graph showing NIR-to-orange upconversion photoluminescence using FDPP and PdPc(OBu)$_8$ is shown in FIG. 3D. FIG. 3E is an exemplary graph showing NIR-to-blue upconversion photoluminescence using TTBP and PtTPTNP.

In considering the energetic requirements of a new infrared-visible triplet fusion upconversion system, it is possible to vary the singlet energy levels of diketopyrrolopyrrole derivatives for singlet fission without altering the triplet energy. In one representative example, the singlet energy was adjusted until it was slightly less than double the triplet energy, which allowed for triplet fusion upconversion. Furanyldiketopyrrolopyrrole (FDPP) was used as an annihilator with palladium(ii) octabutoxyphthalocyanine (PdPc) as the sensitizer. This system absorbed NIR photons (λ max=730 nm) and had an emission that extended to around 530 nm (FIG. 3D). The FDPP:PdPc system had an upconversion yield of 3.2%, while the fluorescence quantum yields of common photoredox catalysts such as [Ru(bpy)$_3$]$^{2+}$ (bpy, bipyridyl) and Rose Bengal are 9.5% and 9%, respectively. When combining the upconversion system with hydrodehalogenation conditions, the dehalogenated product was obtained in 61% yield.

This FDPP:PdPc system enables the use of NIR light to promote reactions that require photocatalysts that absorb green or yellow light. However, most organometallic photocatalysts absorb higher-energy blue or ultraviolet light. It is possible to use the NIR absorbing sensitizer platinum(ii) tetraphenyltetranaphthoporphyrin (PtTPTNP), together with a blue-emitting annihilator, tetratertbutylperylene (TTBP), to generate NIR-to-blue photon upconversion. This system generated a large anti-Stokes shift (around 1.0 eV) and provides an upconversion yield of up to 2.0% (FIG. 3E).

While various exemplary embodiments have been described above, it should be understood that such disclosures have been presented by way of example only and are not limiting. Thus, the breadth and scope of the subject compositions and methods should not be limited by any of the above-described exemplary embodiments, but should be defined only in accordance with the following claims and their equivalents.

Having now fully described the subject compositions and methods, it will be understood by those of ordinary skill in the art that the same can be performed within a wide and equivalent range of conditions, formulations and other parameters without affecting their scope or any embodiment thereof. All cited patents, patent applications, publications, and documents are fully incorporated by reference in their entirety.

EXEMPLARY REFERENCES

The following references are hereby incorporated by reference in their entireties:
[1] Neumann et al., Angew. Chem. Int. Ed., 2011, 50, 951-954.
[2] Mashraqui et al., Tetrahedron Letters, 1985, 26, 1453-1456.
[3] Natarajan et al., Org. Chem Front. 2016, 3, 1265-1270.

The present invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

What is claimed is:
1. A composition, comprising:
a photosensitizer; and
an annihilator able to accept triplet-triplet energy transfer from the photosensitizer, wherein (1) the photosensitizer is PdPc(OBu)$_8$ and the annihilator is FDPP, or (2) the photosensitizer is PtTPTNP and the annihilator is TTBP.
2. The composition of claim 1, further comprising:
a cleavable moiety able to accept energy from the annihilator in the higher energy state to cause cleavage of the cleavable moiety; and
a releasable moiety releasable from the composition upon cleavage of the cleavable moiety.
3. The composition of claim 2, wherein the composition comprises a carrier material comprising the photosensitizer, the annihilator, and the cleavable moiety.
4. The composition of claim 3, wherein the carrier material further comprises the releasable moiety.
5. The composition of claim 4, wherein the carrier material comprises at least one of a polymer, a particle, a film or a polymeric micelle.
6. The composition of claim 4, wherein the particle has an average diameter of less than about 1 mm.
7. The composition of claim 4, wherein the carrier material comprises a film.
8. The composition of claim 4, wherein the releasable moiety is at least one of a drug, a caged species, an anti-angiogenesis drug, TNP-470, Combretastatin A4, an antiinflammatory drug, dexamethasone, an anticancer drug, a chemotherapy drug, doxorubicin, topotecan, or verteporfin.
9. The composition of claim 3, wherein the composition is contained within at least one of a subject, an eye of a subject, a skin of a subject, or a tumor in a subject.
10. A method, comprising:
absorbing a photon in a photosensitizer;
transferring energy from the photosensitizer to an annihilator via triplet-triplet energy transfer;
producing a higher-energy state via triplet-triplet annihilation from the transferred energy in two annihilators;
transferring energy from the annihilator in the higher-energy state to an active moiety via Forster resonance energy transfer; and
causing a chemical reaction in the active moiety using the transferred energy, wherein at least one of (a) the photosensitizer is PdPc (OBu)$_8$ and the annihilator is FDPP, or (b) the photosensitizer is PtTPTNP and the annihilator is TTBP.

11. The method of claim 10, wherein the active moiety is a cleavable moiety, and wherein the chemical reaction is cleavage of the cleavable moiety.

12. The method of claim 11, wherein cleaving the cleavable moiety causes release of a releasable moiety.

13. A method, comprising:
applying, to an eye of a subject, a composition comprising a photosensitizer, an annihilator able to accept triplet-triplet energy transfer from the photosensitizer, and a cleavable moiety able to accept energy from the annihilator in the higher energy state to cause cleavage of the cleavable moiety; and
applying light to at least a portion of the eye to cause cleavage of the cleavable moiety,
wherein at least one of (a) the photosensitizer is PdPc (OBu)$_8$ and the annihilator is FDPP, or (b) the photosensitizer is PtTPTNP and the annihilator is TTBP.

14. The method of claim 13, wherein the light is at least one of coherent or noncoherent.

15. The method of claim 13, wherein the light is applied to an eye at an irradiance of at least one of (i) at least about 1 mW/cm, (ii) at least about 50 mW/cm, or (iii) no more than about 150 mW/cm.

16. The method of claim 13, wherein the subject has or is at risk for at least one of age-related macular degeneration or retinoblastoma.

17. A method, comprising:
applying, to an eye of a subject, a composition comprising a photosensitizer, an annihilator, a cleavable moiety, and a carrier material; and
applying light in at least a portion of the eye, wherein absorption of light by the photosensitizer causes energy transfer to the annihilator and then to the cleavable moiety to cause cleavage of the cleavable moiety,
wherein at least one of (a) the photosensitizer is PdPc (OBu)$_8$ and the annihilator is FDPP, or (b) the photosensitizer is PtTPTNP and the annihilator is TTBP.

18. A method, comprising:
applying, to an eye of a subject, a composition comprising a carrier material comprising a photosensitizer having an absorption, an annihilator able to receive energy from the photosensitizer to produce an upconversion emission having higher energy than the absorption of the photosensitizer, and a cleavable moiety having an absorption overlapping with the upconversion emission from the annihilator; and
applying light to at least a portion of the eye to cause cleavage of the cleavable moiety;
wherein at least one of (a) the photosensitizer is PdPc (OBu)$_8$ and the annihilator is FDPP, or (b) the photosensitizer is PtTPTNP and the annihilator is TTBP.

* * * * *